US011389512B2

(12) United States Patent
Bar-Or et al.

(10) Patent No.: US 11,389,512 B2
(45) Date of Patent: Jul. 19, 2022

(54) USE OF LOW MOLECULAR WEIGHT FRACTIONS OF HUMAN SERUM ALBUMIN IN TREATING DISEASES

(71) Applicant: Ampio Pharmaceuticals, Inc., Englewood, CO (US)

(72) Inventors: David Bar-Or, Englewood, CO (US); Elizabeth Frederick, Denver, CO (US); Melissa Hausburg, Arvada, CO (US)

( * ) Notice: Subject to any disclaimer, the term of this patent is extended or adjusted under 35 U.S.C. 154(b) by 0 days.

(21) Appl. No.: 15/189,839

(22) Filed: Jun. 22, 2016

(65) Prior Publication Data

US 2016/0367644 A1 Dec. 22, 2016

Related U.S. Application Data

(60) Provisional application No. 62/318,873, filed on Apr. 6, 2016, provisional application No. 62/182,985, filed on Jun. 22, 2015.

(51) Int. Cl.
*A61K 38/38* (2006.01)
*A61P 19/02* (2006.01)
*A61P 37/06* (2006.01)

(52) U.S. Cl.
CPC ............ *A61K 38/385* (2013.01); *A61P 19/02* (2018.01); *A61P 37/06* (2018.01)

(58) Field of Classification Search
CPC .................................................. A61K 38/385
See application file for complete search history.

(56) References Cited

U.S. PATENT DOCUMENTS

| | | |
|---|---|---|
| 3,763,091 A | 10/1973 | Crescenzi et al. |
| 3,772,265 A | 11/1973 | Isowa et al. |
| 3,928,330 A | 12/1975 | Ramey et al. |
| 3,941,790 A | 3/1976 | Creighton |
| 3,976,773 A | 8/1976 | Curran |
| 4,006,261 A | 2/1977 | Pickenhagen et al. |
| 4,088,649 A | 5/1978 | Smith et al. |
| 4,205,057 A | 5/1980 | Whitaker |
| 4,289,759 A | 9/1981 | Heavner et al. |
| 4,312,987 A | 1/1982 | Beck |
| 4,331,595 A | 5/1982 | Heavner et al. |
| 4,661,500 A | 4/1987 | Rozencwaig |
| 4,694,061 A | 9/1987 | Pfeifer |
| 4,694,081 A | 9/1987 | Miller et al. |
| 4,771,056 A | 9/1988 | Rozencwaig |
| 4,806,538 A | 2/1989 | Shimazaki et al. |
| 4,886,796 A | 12/1989 | Eichner et al. |
| 4,940,709 A | 7/1990 | Shimazaki et al. |
| 4,992,552 A | 2/1991 | Hubbs et al. |
| 5,047,401 A | 9/1991 | Lipsky et al. |
| 5,144,073 A | 9/1992 | Hubbs |
| 5,238,938 A | 8/1993 | Tone et al. |
| 5,352,461 A | 10/1994 | Feldstein et al. |
| 5,358,938 A | 10/1994 | Cai et al. |
| 5,358,953 A | 10/1994 | Alker et al. |
| 5,418,218 A | 5/1995 | Wilber |
| 5,434,151 A | 7/1995 | Cai et al. |
| 5,463,083 A | 10/1995 | Biftu et al. |
| 5,503,852 A | 4/1996 | Steiner et al. |
| 5,512,544 A | 4/1996 | Wallach et al. |
| 5,538,993 A | 7/1996 | Mechoulam et al. |
| 5,543,402 A | 8/1996 | Bosies et al. |
| 5,543,503 A | 8/1996 | Chuntharapai et al. |
| 5,545,404 A | 8/1996 | Page |
| 5,550,132 A | 8/1996 | Benson et al. |
| 5,561,115 A | 10/1996 | Tenold |
| 5,578,323 A | 11/1996 | Milstein et al. |
| 5,589,501 A | 12/1996 | Carrera et al. |
| 5,648,486 A | 7/1997 | Cai et al. |
| 5,665,714 A | 9/1997 | Paltauf et al. |
| 5,693,338 A | 12/1997 | Milstein |
| 5,700,804 A | 12/1997 | Collins et al. |
| 5,703,093 A | 12/1997 | Cai et al. |
| 5,741,809 A | 4/1998 | Biftu et al. |
| 5,750,530 A | 5/1998 | Bryans et al. |
| 5,750,565 A | 5/1998 | Cai et al. |
| 5,776,892 A | 7/1998 | Counts et al. |
| 5,780,503 A | 7/1998 | Biftu et al. |
| 5,792,776 A | 8/1998 | Biftu et al. |
| 5,811,241 A | 9/1998 | Goodfellow et al. |
| 5,817,751 A | 10/1998 | Szardenings et al. |
| 5,834,032 A | 11/1998 | Song |
| 5,843,950 A | 12/1998 | Tasaka et al. |
| 5,856,323 A | 1/1999 | Cai et al. |
| 5,877,174 A | 3/1999 | Ono et al. |
| 5,883,227 A | 3/1999 | Kline et al. |
| 5,886,152 A | 3/1999 | Nakatani et al. |
| 5,902,812 A | 5/1999 | Brocchini et al. |
| 5,919,785 A | 7/1999 | Dinsmore et al. |
| 5,932,112 A | 8/1999 | Browning, Jr. |
| 5,932,579 A | 8/1999 | Campbell et al. |
| 5,976,569 A | 11/1999 | Milstein |
| 5,985,581 A | 11/1999 | Nixon et al. |
| 5,990,112 A | 11/1999 | Campbell et al. |
| 6,034,057 A | 3/2000 | Dutta |
| 6,034,221 A | 3/2000 | Berezenko et al. |
| 6,060,452 A | 5/2000 | Green et al. |
| 6,090,780 A | 7/2000 | Prasad |
| 6,096,737 A | 8/2000 | Loder |
| 6,099,856 A | 8/2000 | Milstein et al. |
| 6,107,050 A | 8/2000 | Alkon et al. |

(Continued)

FOREIGN PATENT DOCUMENTS

| | | |
|---|---|---|
| CN | 1120439 | 4/1996 |
| CN | 101856345 | 10/2010 |

(Continued)

OTHER PUBLICATIONS

De Souza et al. 2003; Lung tissue remodeling in the acute respiratory distress syndrome. (J. Pneumologia 29(4): 1-14.*

(Continued)

*Primary Examiner* — Karen Cochrane Carlson
(74) *Attorney, Agent, or Firm* — Sheridan Ross P.C.

(57) ABSTRACT

The present invention provides a method of modulating various aspects of the immune system. In particular, the present invention teaches the use of diketopiperazines (DKPs) to modulate various aspects of the immune system such as, for example, inflammation, T-cells and various cytokines.

29 Claims, 5 Drawing Sheets

(56) References Cited

U.S. PATENT DOCUMENTS

| | | |
|---|---|---|
| 6,180,616 B1 | 1/2001 | Fukunaga |
| 6,222,029 B1 | 4/2001 | Edwards et al. |
| 6,248,363 B1 | 6/2001 | Patel et al. |
| 6,262,119 B1 | 7/2001 | Ferrante et al. |
| 6,265,535 B1 | 7/2001 | Greene et al. |
| 6,331,318 B1 | 12/2001 | Milstein et al. |
| 6,358,957 B1 | 3/2002 | Fukumoto et al. |
| 6,395,774 B1 | 5/2002 | Milstein |
| 6,441,172 B1 | 8/2002 | Nefzi et al. |
| 6,461,875 B1 | 10/2002 | Bar-Or et al. |
| 6,475,743 B1 | 11/2002 | Bar-Or et al. |
| 6,492,179 B1 | 12/2002 | Bar-Or et al. |
| 6,531,505 B2 | 3/2003 | Xu et al. |
| 6,541,224 B2 | 4/2003 | Yu et al. |
| 6,555,543 B2 | 4/2003 | Bar-Or et al. |
| 6,635,649 B2 | 10/2003 | Teng et al. |
| 6,677,473 B1 | 1/2004 | Madison et al. |
| 6,689,765 B2 | 2/2004 | Baroudy et al. |
| 6,815,214 B2 | 11/2004 | Boyce et al. |
| 6,930,112 B2 | 8/2005 | Weaver et al. |
| 6,967,202 B2 | 11/2005 | Rao et al. |
| 7,026,322 B2 | 4/2006 | Hayashi et al. |
| 7,175,844 B2 | 2/2007 | King |
| 7,276,534 B2 | 10/2007 | Milstein |
| 7,288,545 B2 | 10/2007 | Teng et al. |
| 7,332,153 B2 | 2/2008 | Bhatia et al. |
| 7,378,403 B2 | 5/2008 | Kozikowski et al. |
| 7,575,929 B2 | 8/2009 | Bar-Or et al. |
| 7,732,403 B2 | 6/2010 | Bar-Or et al. |
| 7,919,497 B2 | 4/2011 | Palladino et al. |
| 8,030,488 B2 | 10/2011 | Sviridov et al. |
| 8,067,425 B2 | 11/2011 | Brimble et al. |
| 8,183,209 B2 | 5/2012 | Bar-Or et al. |
| 8,198,407 B1 | 6/2012 | Burton et al. |
| 8,217,047 B2 | 7/2012 | Bar-Or |
| 8,268,830 B2 | 9/2012 | Bar-Or et al. |
| 8,314,106 B2 | 11/2012 | Kraft |
| 8,324,167 B2 | 12/2012 | Bar-Or et al. |
| 8,383,124 B2 | 2/2013 | Zheng |
| 8,440,696 B2 | 5/2013 | Bar-Or et al. |
| 8,455,517 B2 | 6/2013 | Bar-Or et al. |
| 8,507,496 B2 | 8/2013 | Bar-Or |
| 8,513,196 B2 | 8/2013 | Bar-Or et al. |
| 8,551,953 B2 | 10/2013 | Bar-Or et al. |
| 8,841,307 B2 | 9/2014 | Bar-Or et al. |
| 8,871,772 B2 | 10/2014 | Bar-Or |
| 8,916,568 B2 | 12/2014 | Bar-Or et al. |
| 8,962,568 B2 | 2/2015 | Bar-Or et al. |
| 8,969,308 B2 | 3/2015 | Bar-Or et al. |
| 8,980,834 B2 | 3/2015 | Bar-Or et al. |
| 9,034,878 B2 | 5/2015 | Bar-Or |
| 9,060,968 B2 | 6/2015 | Bar-Or et al. |
| 2002/0123505 A1 | 9/2002 | Mollison et al. |
| 2003/0119750 A1 | 6/2003 | Demuth et al. |
| 2003/0153575 A1 | 8/2003 | Orme et al. |
| 2003/0157030 A1 | 8/2003 | Davis et al. |
| 2003/0187226 A1 | 10/2003 | Goddey et al. |
| 2003/0203915 A1 | 10/2003 | Fang et al. |
| 2004/0024180 A1 | 2/2004 | Drauz et al. |
| 2004/0038865 A1 | 2/2004 | Gelber et al. |
| 2004/0063654 A1 | 4/2004 | Davis et al. |
| 2005/0096323 A1 | 5/2005 | Cheng et al. |
| 2005/0249681 A1 | 11/2005 | Heidenfelder et al. |
| 2007/0060508 A1 | 3/2007 | Haberl et al. |
| 2007/0208087 A1 | 9/2007 | Sanders et al. |
| 2008/0009507 A1 | 1/2008 | Cosford et al. |
| 2008/0017576 A1 | 1/2008 | Belfort et al. |
| 2008/0260838 A1 | 10/2008 | Hokenson et al. |
| 2009/0038416 A1 | 2/2009 | Bonner |
| 2010/0042206 A1 | 2/2010 | Yadav et al. |
| 2010/0120056 A1 | 5/2010 | Bar-Or et al. |
| 2010/0144611 A1 | 6/2010 | Bar-Or et al. |
| 2010/0190696 A1 | 7/2010 | Bar-Or et al. |
| 2010/0240602 A1 | 9/2010 | Burke et al. |
| 2012/0058934 A1 | 3/2012 | Bar-Or |
| 2012/0094918 A1 | 4/2012 | Bar-Or et al. |
| 2012/0220530 A1 | 8/2012 | Plumridge et al. |
| 2013/0079284 A1 | 3/2013 | Bar-Or et al. |
| 2014/0286913 A1 | 9/2014 | Bar-Or et al. |
| 2014/0294738 A1 | 10/2014 | Bar-Or |
| 2014/0302114 A1 | 10/2014 | Bar-Or |
| 2015/0051223 A1 | 2/2015 | Bar-Or et al. |
| 2015/0051224 A1 | 2/2015 | Bar-Or |
| 2015/0352175 A1 | 12/2015 | Bar-Or et al. |
| 2015/0366932 A1 | 12/2015 | Bar-Or |
| 2016/0015705 A1 | 1/2016 | Bar-Or et al. |
| 2016/0045493 A1 | 2/2016 | Bar-Or |
| 2017/0209433 A1 | 7/2017 | Bar-Or et al. |
| 2017/0274039 A1 | 9/2017 | Bar-Or et al. |
| 2018/0140598 A1 | 5/2018 | Bar-Or et al. |

FOREIGN PATENT DOCUMENTS

| | | |
|---|---|---|
| CS | 254868 | 6/1987 |
| CZ | 2827.94 | 4/1996 |
| CZ | 280726 | 4/1996 |
| CZ | 2000-2680 | 7/2000 |
| CZ | 2000-2681 | 7/2000 |
| DE | 19937721 | 2/2001 |
| EP | 0043219 | 1/1982 |
| EP | 0214557 | 3/1987 |
| EP | 0216746 | 4/1987 |
| EP | 0220958 | 5/1987 |
| EP | 0493812 | 7/1992 |
| EP | 0557388 | 9/1993 |
| EP | 0610943 | 8/1994 |
| EP | 0655060 | 5/1995 |
| EP | 0835660 | 4/1998 |
| EP | 0939124 | 9/1999 |
| EP | 1445323 | 8/2004 |
| FR | 2717484 | 9/1995 |
| GB | 2263109 | 7/1993 |
| GB | 2372740 | 9/2002 |
| JP | S52-25019 | 2/1977 |
| JP | S57-32272 | 2/1982 |
| JP | S59-73574 | 4/1984 |
| JP | S61-112060 | 5/1986 |
| JP | S62-036331 | 2/1987 |
| JP | S63-290868 | 11/1988 |
| JP | H01-013075 | 1/1989 |
| JP | 3176478 | 7/1991 |
| JP | H05-163148 | 6/1993 |
| JP | H07-247474 | 9/1995 |
| JP | H08-277203 | 10/1996 |
| JP | H10-226615 | 8/1998 |
| JP | H10-245315 | 9/1998 |
| JP | H11-504509 | 4/1999 |
| JP | 2000-327575 | 11/2000 |
| JP | 2001-055340 | 2/2001 |
| JP | 2008-505084 | 2/2008 |
| JP | 2009-508658 | 3/2009 |
| JP | 2010-508971 | 3/2010 |
| JP | 2011-507609 | 3/2011 |
| NZ | 218088 | 1/1989 |
| NZ | 335544 | 8/2001 |
| RU | 2112242 | 5/1998 |
| RU | 2125728 | 1/1999 |
| RU | 2128840 | 4/1999 |
| WO | WO 91/14378 | 10/1991 |
| WO | WO 93/08815 | 5/1993 |
| WO | WO 94/04512 | 3/1994 |
| WO | WO 94/04513 | 3/1994 |
| WO | WO 94/04537 | 3/1994 |
| WO | WO 94/20063 | 9/1994 |
| WO | WO 95/03054 | 2/1995 |
| WO | WO 95/18610 | 7/1995 |
| WO | WO 96/00212 | 1/1996 |
| WO | WO 96/00391 | 1/1996 |
| WO | WO 96/10396 | 4/1996 |
| WO | WO 96/14317 | 5/1996 |
| WO | WO 96/32478 | 10/1996 |
| WO | WO 97/12625 | 4/1997 |
| WO | WO 97/36888 | 10/1997 |
| WO | WO 97/38011 | 10/1997 |

(56) References Cited

FOREIGN PATENT DOCUMENTS

| WO | WO 97/48685 | 12/1997 |
| --- | --- | --- |
| WO | WO 98/09968 | 3/1998 |
| WO | WO 98/40748 | 9/1998 |
| WO | WO 99/40931 | 8/1999 |
| WO | WO 99/49865 | 10/1999 |
| WO | WO 99/51256 | 10/1999 |
| WO | WO 99/51720 | 10/1999 |
| WO | WO 00/20454 | 4/2000 |
| WO | WO 00/20840 | 4/2000 |
| WO | WO 00/22439 | 4/2000 |
| WO | WO 00/43000 | 7/2000 |
| WO | WO 00/057187 | 9/2000 |
| WO | WO 01/34586 | 5/2001 |
| WO | WO 01/64241 | 9/2001 |
| WO | WO 01/91713 | 12/2001 |
| WO | WO 02/011676 | 2/2002 |
| WO | WO 02/012201 | 2/2002 |
| WO | WO 02/059604 | 8/2002 |
| WO | WO 02/062797 | 8/2002 |
| WO | WO 02/083667 | 10/2002 |
| WO | WO 02/089738 | 11/2002 |
| WO | WO 03/032809 | 4/2003 |
| WO | WO 03/045395 | 6/2003 |
| WO | WO 2004/005292 | 1/2004 |
| WO | WO 2004/034060 | 4/2004 |
| WO | WO 2004/048345 | 6/2004 |
| WO | WO 2004/054498 | 7/2004 |
| WO | WO 2005/011699 | 2/2005 |
| WO | WO 2006/023943 | 3/2006 |
| WO | WO 2007/098500 | 8/2007 |
| WO | WO 2007/121411 | 10/2007 |
| WO | WO 2007/149730 | 12/2007 |
| WO | WO 2008/008357 | 1/2008 |
| WO | WO 2009/009793 | 1/2009 |
| WO | WO 2009/032651 | 3/2009 |
| WO | WO 2009/042193 | 4/2009 |
| WO | WO 2010/102148 | 9/2010 |
| WO | WO 2012/033789 | 3/2012 |
| WO | WO 2012/174472 | 12/2012 |
| WO | 2013055734 A1 * | 4/2013 |
| WO | WO 2015/028657 | 3/2015 |

OTHER PUBLICATIONS

"CENTRICON Centrifugal Filter Devices User Guide," Millipore Corp., Mar. 2005, 23 pages.
Cytokines and Autoimmune Diseases, edited by Kuchroo, et al., 2002, Humana Press Inc., Totowa, NJ, pp. 3-23, 389-406.
Cytokines and Autoimmune Diseases, edited by Kuchroo, et al., 2002, Humana Press Inc., Totowa, NJ, pp. 5, 11, and 391.
Database WPI Section Ch, Week 199844 Derwent Publications Ltd., London, GB; Class B03, AN 1998-515050 XP002369751 & JP 10 226615 A (Pola Chem Ind Inc) Aug. 25, 1998 (Aug. 25, 1998).
"Diabetic Retinopathy—What you should know," National Institutes of Health, 2003, NIH Publication No. 06-2171, 24 pages.
"Disposable PD-10 Desalting Columns," GE Healthcare Life Sciences, downloaded Nov. 1, 2011, 2 pages.
"Desalting and buffer exchange with Sephadex® G-25," Amersham Biosciences, downloaded from www.gelifesciences.com on Jan. 8, 2013, 8 pages.
"Human Albumin," Sigma downloaded from www.sigmaaldrich.com on Jan. 8, 2013, 1 page.
Online Medical Dictionary definition of albumin, medical-dictionary.thefreedictionary.com/albumin, downloaded Nov. 1, 2011, 4 pages.
The Cytokine Handbook, edited by Thomson and Lotze, 4th edition, 2003 Academic Press, vol. I, London, UK, pp. 169, 186, 187, 467, 570, 571, 838, 839, 1189-1193, 1197-1200.
The Cytokine Handbook, edited by Thomson and Lotze, 4th edition, 2003 Academic Press, vol. II, London, UK, pp. 838-860 and 1189-1211.
The Cytokine Handbook, edited by Thomson and Lotze, 4th edition, 2003 Academic Press, vol. I, London, UK, pp. 167-199, 456-474, 567-601.
The Dictionary of IMMUNOLOGY, Fourth Edition, Edited by Herbert et al., 1995, pp. 51-52 and 69.
"Tryprostatin A, Aspergillus fumigates," available at www.emdbiosciences.com/Products/ProductDisplay.asp?catno=649305&, printed on Jun. 21, 2006, 1 page.
Abraha et al., "C-terminal inhibition of tau assembly in vitro and in Alzheimer's disease," Journal of Cell Science, 2000, vol. 113, pp. 3737-3745.
Acharya et al., "Solid-phase synthesis of substituted imidazoline-tethered 2,3-diketopiperazines, cyclic ureas, and cyclic thioureas," J Comb Chern, Nov.-Dec. 2001, vol. 3(6), pp. 612-623.
Adorini, L., "Selective immunointervention in autoimmune diseases: lessons from multiple sclerosis," J Chemother, Jun. 2001, vol. 13(3), pp. 219-234 (Abstract Only Provided).
Akiyama et al., "Inflammation and Alzheimer's disease," Neurobiol Aging, 2000, vol. 21, pp. 383-421.
Albert et al., "ABT-491, a highly potent and selective PAF antagonist, inhibits nasal vascular permeability associated with experimental allergic rhinitis in Brown Norway rats," Inflamm. Res., 1997, Supplement 2, pp. S133-S134.
Alvarez et al., "Isolation and Structure Elucidation of Two New Calpain Inhibitors from Streptomyces Griseus," J. Antibiotics, Nov. 1994, vol. 47(11), pp. 1195-1201.
Amoako et al., "Osteoarthritis in Young, Active, and Athletic Individuals," Clinical Medicine Insights: Arthritis and Musculoskeletal Disorders, 2014, vol. 7, pp. 27-32.
Andreasen et al., "Cerebrospinal fluid beta-amyloid (1-42) in Alzheimer disease: differences between early-and late-onset Alzheimer disease and stability during the course of disease," Arch. Neurol., Jun. 1999, vol. 56(6), pp. 673-680.
Arbabi et al., "Priming Interleukin 8 Production: Role of Platelet-Activating Factor and p38," Arch Surg., Dec. 1999, vol. 134(12), pp. 1348-1353.
Ashwood et al. "Is autism an autoimmune disease?" Autoimmunity Reviews, Nov. 2004, vol. 3, No. 7-8, pp. 557-562.
Au et al., "Effect of PDE4 Inhibitors on Zymosan-Induced IL-8 Release From Human Neutrophils: Synergism with Prostanoids and Salbutamol," Br. J. Pharmacol, 1998, vol. 123, pp. 1260-1266.
Bagaria et al., "Cyclo(L-leucyl-alpha,beta-dehydrophenylalanine): the first diketopiperazine containing an alpha,beta-dehydrophenylalanine residue," Acta Crystallogr C., Mar. 2005, vol. 61(Pt 3), pp. 174-176, Epub Feb. 28, 2005.
Baig et al., "High Performance Liquid Chromatography as a Tool in the Definition of Abnormalities in Monamine and Tryptophan Metabolites in Cerebrospinal Fluid from Patients with Neurological Disorders," Biomed Chromatogr 1991, 5(3):108-112 (Abstract Only Provided).
Balk, "Lesson 24, vol. 12—ARDS: Pathophysiology of SIRS and MODS" www.chestnet.org/education/pccu/vol12/ lesson24.html, pp. 1-19, printed Jul. 20, 2000.
Banks et al., "Radioactively Iodinated Cyclo(His-Pro) Crosses the Blood-Brain Barrier and Reverses Ethanol-Induced Narcosis," Am J Physiol, May 1993, vol. 264(5 Pt. 1), pp. E723-E729 (Abstract Only Provided).
Bar-Or et al. "Commercial human albumin preparations for clinical use are immunosuppressive in vitro," Critical Care Medicine, Jun. 2006, vol. 34, No. 6, pp. 1707-1712.
Bar-Or et al., "A Randomized Clinical Trial to Evaluate Two Doses of an Intra-Articular Injection of LMWF-5A in Adults with Pain Due to Osteoarthritis of the Knee," PLoS One, 2014, vol. 9, Iss. 2, e87910, 8 pages.
Bar-Or et al., "An Analog of the Human Albumin N-Terminus (Asp-Ala-His-Lys) Prevents Formation of Copper-Induced Reactive Oxygen Species," Biochemical and Biophysical Research Communications, 2001, vol. 284(3), pp. 856-862.
Bar-Or et al., "Dipeptidyl peptidase IV activity in commercial solutions of human serum albumin" Analytical Biochemistry, 2013, vol. 441, Iss. 1, pp. 13-17.
Bar-Or et al., "Low Molecular Weight Fraction of Commercial Human Serum Albumin Induces Morphologic and Transcriptional Changes of Bone Marrow-Derived Mesenchymal Stem Cells," Stem Cells Translational Medicine, 2015, vol. 4, No. 8, pp. 945-955.

(56) References Cited

OTHER PUBLICATIONS

Bar-Or et al., "Potential Plasma Surrogate Biomakers for CNS Demyelinating Processes," 19th Congress of the European Committee for Treatment and Research in Multiple Sclerosis Meeting; Sep. 17-20, 2003; 2 pp. (Abstract first distributed at the meeting; attached is poster presented at meeting).
Barrow et al., WIN 64821, a New Competitive Antagonist to Substance P, Isolated from an Aspergillus Species: Structure Determination and Solution Conformation, J. Org. Chem., 1993, vol. 58, pp. 6016-6021.
Battersby et al., "Diketopiperazine Formation and N-Terminal Degradation in Recombinant Human Growth Hormone," Int. J. Pept. Protein Res, Sep. 1994, vol. 44(3), pp. 215-222 (Abstract Only Provided).
Berman et al., "Psoriasis," PubMed Health, reviewed Nov. 22, 2011, available at www.ncbi.nlm.nih.gov/pubmedhealth/PMH0001470/?report=printable.
Berry et al., "Inhibition of Tau Polymerization by its Carboxy-Terminal Caspase Cleavage Fragment," Biochemistry, 2003, vol. 42, pp. 8325-8331.
Bhargava et al., "Inhibition of Neuroleptic-Induced Dopamine Receptor Supersensitivity by Cyclo (Leu-Gly)," Pharmacol Biochem Behav, Nov. 1980, vol. 13(5), pp. 633-636 (Abstract Only Provided).
Bhargava, "Antagonism of ketamine-induced anesthesia and hypothermia by thyrotropin releasing hormone and cyclo (His-Pro)," Neuropharmacology, 1981, vol. 20(7), pp. 699-702.
Bhargava, "Inhibition of abstinence syndrome in opiate dependent mice by cyclo (His-Pro)," Life Sci, 1981, vol. 28(11), pp. 1261-1267.
Bhargava, "The effect of melanotrophin release inhibiting factor (MIF) and cyclo (Leu-Gly) on the tolerance to morphine-induced antinociception in the rat: a dose-response study," Br J Pharmacol, Apr. 1981, vol. 72(4) (Abstract Only Provided).
Bhargava, "The effects of thyrotropin releasing hormone and histidyl-proline diketopiperazine on delta-9-tetrahydrocannabinol-induced hypothermia," Life Sci, 1980, vol. 26(11), pp. 845-850.
Bielekova et al., "Development of biomarkers in multiple sclerosis," Brain, Jul. 2004, vol. 127(Pt 7), pp. 1463-1478, Epub Jun. 4, 2004.
Binisti et al., "Structure-Activity Relationships in Platelet Activating Factor," J. Lipid Mediat. Cell Signal, Jan. 1997, vol. 15(2), pp. 125-144 (Abstract Only Provided).
Blazickova et al., "Immunomodulatory Characteristics of Synthetic Cyclic Dipeptides," Int. J. Immunotherapy, 1994, vol. 10(3), pp. 89-93.
Borthwick, "2,5-Diketopiperazines: Synthesis, Reactions, Medicinal Chemistry, and Bioactive Natural Products," Chemical Reviews, 2012, vol. 112, Iss. 7, pp. 3641-3716.
Botting, "Vane's discovery of the mechanism of action of aspirin changed our understanding of its clinical pharmacology," Pharmacological Reports, 2010, vol. 62, Iss. 3, pp. 518-525.
Bowden et al., "Re-evaluation of histidyl-proline diketopiperazine [cyclo (His-Pro)] effects on food intake in the rate," Pharmacol. Biochem. Behav., Feb. 1988, vol. 29(2), pp. 357-363 (Abstract Only Provided).
Brauns et al., "Selected cyclic dipeptides inhibit cancer cell growth and induce apoptosis in HT-29 colon cancer cells," Anticancer Research, 2004, vol. 24, pp. 1713-1720.
Bressan et al., "Coordination chemistry of peptides. Part II. Crystal structure of cyclo-L-methionylglycine and studies of metal complexation," Int J Pept Protein Res, Apr. 1982, vol. 19(4) (Abstract Only Provided).
Bresser et al., "T-Cell Activation in the Lungs of Patients With Systemic Sclerosis and Its Relation With Pulmonary Fibrosis," Chest, Jul. 2001, 6 pages.
Brittberg et al., "Treatment of Deep Cartilage Defects in the Knee with Autologous Chondrocyte Transplantation," The New England Journal of Medicine, 1994, vol. 331, No. 14, pp. 889-895.

Brown et al., "Anti-VEGF Agents in the Treatment of Neovascular Age-related Macular Degeneration: Applying Clinical Trial Results to the Treatment of Everyday Patients," American Journal of Opthalmology, 2007, vol. 144, Iss. 4, pp. 627-637.
Buckley et al., "Proresolving Lipid Mediators and Mechanisms in the Resolution of Acute Inflammation," Immunity, 2014, vol. 40, Iss. 3, pp. 315-327.
Bunn, "Early detection of lung cancer using serum RNA or DNA markers: ready for "prime time" or for validation?," J Clin Oncol., Nov. 1, 2003, vol. 21(21), pp. 3891-3893.
Caballero et al., "Brief synthesis of the cell cycle inhibitor tryprostatin B and its alanine analogue," Fourth International Electronic conference of Synthetic Organic Chemistry (ECXOC-4), Sep. 1-13, 2000, 4 pages, available at pages.unibas.ch/mdpi/eecxoc-4/c0023/c0023.htm.
Caballero et al., "Brief total synthesis of the cell cycle inhibitor tryprostatin B and related preparation of its alanine analogue," J Org Chem, Sep. 5, 2003, vol. 68(18) (Abstract Only Provided).
Carlton et al., "Attenuation of alcohol-induced hypothermia by cycle (His-Pro) and its analogs," Neuropeptides, Jun. 1995, vol. 28(6), pp. 351-355 (Abstract Only Provided).
Chan, "Chapter 9: Transplant Rejection and Its Treatment," Atlas of Diseases of the Kidney, vol. 5, (Ed.Henrich et al.), Wiley-Blackwell, 1999, pp. 9.1-9.13.
Chan et al., "Site-Specific N-Terminal Auto-Degradation of Human Serum Albumin," Eur. J. Biochem., 1995, vol. 227, pp. 524-528.
Chen et al., "Up-regulation of Platelet-activating Factor Receptors in Lung and Alveolar Macrophages in the Bleomycin-Hamster Model of Pulmonary Fibrosis," J. Pharmacol. Exp. Ther., 1997, vol. 280(3), pp. 1219-1227.
Cho et al., "Contribution of Natural Inhibitors to the Understanding of the PI3K/PDK1/PKB Pathway in the Insulin-mediated Intracellular Signaling Cascade," Int. J. Mol. Sci., 2008, vol. 9, pp. 2217-2230.
Ciarkowski et al., "Conformation of cyclo-(D-phenylalanyl-trans-4-fluoro-D-prolyl)," Int. J. Pept. Protein Res., vol. 36, Sep. 1990, pp. 285-291.
Clark et al., "Roquefortine E, a Diketopiperazine from an Australian Isolate of Gymnoascus reessii," J. Nat. Prod., 2005, vol. 68(11), p. 1661-1664 (Abstract Only Provided).
Cody et al., "The design of potent and selective inhibitors of thrombin utilizing a piperazinedione template: part 2," Bioorg Med Chem Lett, Sep. 6, 1999, vol. 9(17), pp. 2503-2508.
Coggins et al., "High Affinity Specific Binding of the Thyrotrophin Releasing Hormone Metabolite Histidylproline to Rat Brain Membranes," Neuropeptides, Jan. 1987, vol. 9(1), pp. 83-91 (Abstract Only Provided).
Costa et al., "Aggregation of features of the metabolic syndrome is associated with increased prevalence of chronic complications in Type 2 diabetes," Diabetic Medicine, 2004, vol. 21, Iss. 3, 252-255.
Couladouros et al., "Solid-phase total synthesis of (-)-Phenylhistine and (-)-Aurantiamine. Synthesis of a diverse dehydro-2,5-diketopiperazine library. Part II," Mol Divers., 2005, vol. 9(1-3), pp. 111-121.
Crowe et al., "The N Terminal Region of Human Tau is Present in Alzheimer's Disease Protein A68 and is Incorporated into Paired Helical Filaments," American Journal of Pathology, 1991, vol. 139(6), pp. 1463-1470.
Cruse et al., "Illustrated Dictionary of Immunology" Second Edition, 2003, pp. 192, 260, 530-531.
Cui et al., "Novel Mammalian Cell Cycle Inhibitors, Tryprostatins A, B and Other Diketopiperazines Produced by Aspergillus fumigatus II. Physico-chemical properties and Structures," The Journal Of Antibiotics, Jun. 1996, pp. 534-540.
D'Alagni et al. "Effect of Urea on the Optical Rotatory Dispersion of Diketopiperazines of l-Serine, l-Alanine, l-Lysine, l-Valine, and l-Valylglycine." The Journal of Biological Chemistry, Nov. 10, 1969, vol. 244, No. 21, pp. 5843-5848.
Davidson et al., "Autoimmune Diseases," N. Engl. J. Med, 2001, vol. 345(5), pp. 340-350.

(56) References Cited

OTHER PUBLICATIONS

De La Cruz et al, "Effect of WEB 2086-BS, an antagonist of platelet-activating factor receptors, on retinal vascularity in diabetic rats," European Journal of Pharmacology, 1998, vol. 360, Iss. 1, pp. 37-42.
Degrassi et al., "Plant Growth-Promoting Pseudomonas putida WCS358 Produces and Secretes Four Cyclic Dipeptides: Cross-Talk with Quorum Sensing Bacterial Sensors," Current Microbiology, 2002, vol. 45, pp. 250-254.
Del Fresno et al. "Solid-phase synthesis of diketopiperazines, useful scaffolds for combinatorial chemistry," Tetrahedron Letters, 1998, vol. 39, Iss. 17, pp. 2639-2642.
Denault et al., "Transcriptional activation of the interleukin-8 gene by platelet-activating factor in human peripheral blood monocytes," Immunology, 1997, vol. 91, pp. 297-302.
Diamanti et al., "Distribution and Characterization of Cyclo (His-Pro)-like Immunoreactivity in the Human Gastrointestinal Tract," Neuropeptides, Mar. 1985, vol. 6(1):21-5 (Abstract Only Provided).
Dirr, K. et al., "The transformation of arginine into citrulline," Z. Physiol. Chem., 1935, vol. 237, pp. 121-130.
Duntas et al., "A Fast Protein Liquid Chromatography (FPLC) Method for Study of Thyrotropin-releasing Hormone (TRH) and its metabolite Histidyl-Proline Diketopiperazine (CHP) in Human Blood: Degradation in Liver and Pancreatic Diseases," Neuropeptides, 1993, vol. 25(6), pp. 357-361 (Abstract Only Provided).
Esposito et al., "The Solution Structure of the C-Terminal Segment of Tau Protein," Journal of Peptide Science, 2000, vol. 6, pp. 550-559.
Evans et al. "Metabolic effects of platelet-activating factor in rats in vivo: Stimulation of hepatic glycogenolysis and lipogenesis." Biochemical Journal, Jul. 1990, vol. 269, No. 1, pp. 269-272.
Faden et al., "Neuroprotective and nootropic actions of a novel cyclized dipeptide after controlled cortical impact injury in mice." J. Cerebral Blood Flow & Metabolism, 2003, vol. 23, pp. 355-363.
Faden et al., "Novel diketopiperazine enhances motor and cognitive recovery after traumatic brain injury in rats and shows neuroprotection in vitro and in vivo," J. Cerebral Blood Flow & Metabolism, 2003, vol. 23, pp. 342-354.
Faden et al., "Novel neuroprotective Tripeptides and Dipeptides," Ann. N.Y. Acad. Sci, 2005, vol. 1053, pp. 472-481.
Faden et al., "Novel small peptides with neuroprotective and nootropic properties," J. Alzheimer's Dis, 2004, vol. 6, pp. S93-S97.
Faden et al., "Novel TRH analog improves motor and cognitive recovery after traumatic brain injury in rodents," Am J Physiol, Oct. 1999, vol. 277(4 Pt 2), pp. R1196-R1204.
Falorni et al. "Chiral ligands containing heteroatoms. 11. Optically active 2-hydroxymethyl piperazines as catalysts in the enantioselective addition of diethylzinc to benzaldehyde," Tetrahedron: Asymmetry, 1993, vol. 4, Iss. 11, pp. 2389-2398.
Falorni et al. "Chiral ligands containing heteroatoms. 11. Optically active 2-hydroxymethyl piperazines as catalysts in the enantioselective addition of diethylzinc to benzaldehyde," Tetrahedron: Asymmetry, 1993, vol. 4, Iss. 11, pp. 2389-2398. (Abstract and Graphic only).
Fdhila et al., "dd-diketopiperazines: antibiotics active against Vibrio anguillarum isolated form marine bacteria associated with cultures of Pecten maximus" J Nat Prod, Oct. 2003, vol. 66(10) (Abstract Only Provided).
Fischer, "Diketopiperazines in Peptide and Combinatorial Chemistry," Journal of Peptide Science, 2003, vol. 9, pp. 9-35.
Folkes et al., "Synthesis and in vitro evaluation of a series of diketopiperazine inhibitors of plasminogen activator inhibitor-1," Bioorg Med Chem Lett, Oct. 2001, vol. 11(19), pp. 2589-2592 (Abstract Only Provided).
Fragner et al., "A New Biological Contribution of Cyclo(His-Pro) to the Peripheral Inhibition of Pancreatic Secretion," Am J Physiol, Dec. 1997, vol. 273(6 Pt. 1), pp. E1127-E1132 (Abstract Only Provided).
Gamblin et al., "Tau Polymerization: Role of the Amino Terminus," Biochemistry, 2003, vol. 42(7), pp. 2252-2257.

Garcia-Sierra et al., "Conformational Changes and Truncation of Tau Protein during Tangle Evolution in Alzheimer's Disease," Journal of Alzheimer's Disease, 2003, vol. 5, pp. 65-77.
Gilroy et al., "Inducible cyclooxygenase may have anti-inflammatory properties," Nature Medicine, 1999, vol. 5, Iss. 6, pp. 698-701.
Gomez et al., "Low-Dose Dopamine Agonist Administration Blocks Vascular Endothelial Growth Factor (VEGF)-Mediated Vascular Hyperpermeability without Altering VEGF Receptor 2-Dependent Luteal Angiogenesis in a Rat Ovarian Hyperstimulation Model," Endocrinology, 2006, vol. 147, No. 11, pp. 5400-5411.
Goolcharran et al., "Comparison of the Rates of Deamidation, Diketopiperazine Formation and Oxidation in Recombinant Human Vascular Endothelial Growth Factor and Model Peptides," AAPS PharmSci, 2000 Vol. 2(1), p. E5 (Abstract Only Provided).
Gorbitz "Crystal and Molecular Structure of cyclo-L-Aspartyl-L-alanyl (3,6-Dioxo-5-methyl-2-piperazineacetic acid)" Acta Chemica Scandinavica B, 1987, vol. 41, pp. 83-86.
Gorbitz, "Crystal and molecular structures of the isomeric dipeptides alpha-L-aspartyl-L-alanine and beta-L-aspartyl-L-alanine," Acta Chem Scand B., vol. 41(9), Oct. 1987, pp. 679-685.
Gordon et al, "Reductive Alkylation on a Solid Phase: Synthesis of a Piperazinedione Combinatorial Library," Bioorganic & Medicinal Chemistry Letters, 1995, vol. 5, No. 1, p. 47-50.
Gountopoulou et al. "TNFα is a potent inducer of platelet-activating factor synthesis in adipocytes but not in preadipocytes. Differential regulation by PI3K." Cytokine, Jan. 2008, vol. 41, No. 2 p. 174-181, (Abstract Only).
Granero-Moltó et al., "Regenerative Effects of Transplanted Mesenchymal Stem Cells in Fracture Healing," Stem Cells, 2009, vol. 27, Iss. 8, pp. 1887-1898.
Graz et al "Cyclic Dipeptides in the Induction of Maturation for Cancer Therapy," J. Pharm. Pharmacol., 2000, vol. 52, pp. 75-82.
Graz et al., "Mechanism of a anti-fungal action of selected cyclic dipeptides," Pharmazie, Nov. 2001, vol. 56(11), pp. 900-901.
Gross et al., "Regulation of lnterleukin-8 Production in a Human Colon Epithelial Cell Line (HT-29)," Gastroenterology, 1995, vol. 108, pp. 653-661.
Grubek-Jaworska et al., "CD4/CD8 lymphocytes in BALF during the efferent phase of lung delayed-type hypersensitivity reaction induced by single antigen inhalation," Med Sci Monit, Sep.-Oct. 2001, vol. 7(5), pp. 878-883 (Abstract Only Provided).
Gu et al., "Diketopiperazine Formation, Hydrolysis, and Epimerization of the New Dipeptide Angiotensin-Converting Enzyme Inhibitor RS-10085," Pharm Res, 1987, vol. 4(5), pp. 392-397 (Abstract Only Provided).
Gudasheva et al., "Anxiolytic activity of endogenous nootropic dipeptide cycloprolylglycine in elevated plus-maze test," Bull Exp Biol Med, May 2001, vol. 131(5) (Abstract Only Provided).
Gudasheva et al., "Identification of a novel endogenous memory facilitating cyclic dipeptide cyclo-prolylglycine in rat brain," FEBS Lett, Aug. 5, 1996, vol. 391(1-2) (Abstract Only Provided).
Guerra et al., "PEGylation Prevents the N-Terminal Degradation of Megakaryocyte Growth and Development Factor," Pharm Res, 1998, vol. 15(12), pp. 1822-1827 (Abstract Only Provided).
Gustafson, "Adipose Tissue, Inflammation and Atherosclerosis," J. Atheroscler. Thromb., Apr. 30, 2010, vol. 17(4), pp. 332-341.
Hansel et al. "Metabolic Syndrome Is Associated with Elevated Oxidative Stress and Dysfunctional Dense High-Density Lipoprotein Particles Displaying Impaired Antioxidative Activity." The Journal of Clinical Endocrinology & Metabolism, Oct. 2004, vol. 89, No. 10, pp. 4963-4971.
Harada et al., "Essential involvement of interleukin-8 (IL-8) in acute inflammation," Journal of Leukocyte Biology, 1994, vol. 56, Iss. 5, pp. 559-564.
Hasegawa et al., "Protein Sequence and Mass Spectrometric Analysis of Tau in the Alzheimer's Disease Brain," Journal of Biological Chemistry, 1992, vol. 267(24), pp. 17047-17054.
Hayashi et al., "Synthetic Hexa-and Heptapeptides That Inhibit IL-8 from Binding to and Activating Human Blood Neutrophils1," J. Immunol., 1995, vol. 154, pp. 814-824.

(56) References Cited

OTHER PUBLICATIONS

He et al., "Evidence for a Role of Platelet-Activating Factor (PAF) in the Pathogenesis of Age-Related Macular Degeneration (AMD)", Investigative Ophthalmology & Visual Science, 2007, vol. 48, Iss. 13, 2 pages. (Abstract only).

Hilton et al., "Food Contains the Bioactive Peptide, Cyclo(His-Pro)," J. Clin Endocrinol Metab, Aug. 1992, vol. 75(2), pp. 375-378 (Abstract Only Provided).

Hilton et al., "Identification and Characterization of Cyclo (His-Pro)-Like Immunoreactivity in Amniotic Fluid," Peptides, Mar.-Apr. 1989, vol. 10(2), pp. 299-301 (Abstract Only Provided).

Hilton et al., "Radioimmunoassay of Cyclo(His-Pro) in Unextracted Human Plasma: Report of a Normal Range and Definition of Factors Critical for Successful Assay," Neuropeptides, 1989, vol. 13(1), pp. 65-70 (Abstract Only Provided).

Hilton et al., "Relationship between Plasma Cyclo (His-Pro), a Neuropeptide Common to Processed Protein-Rich Food, C-Peptide/Insulin Molar Ratio in Obese Women," Nutr Neurosci, 2001, vol. 4(6), pp. 469-474 (Abstract Only Provided).

Hlinak et al., "Effect of alaptide, its analogues and oxiracetam on memory for an elevated plus-maze in mice," European Journal of Pharmacology, 1996, vol. 314, pp. 1-7.

Hoffman et al., "An Enzymatically Stable Peptide with activity in the Central Nervous System: Its Penetration through the Blood-CSF Barrier," Brain Res, Feb. 11, 1977, vol. 122(1), pp. 87-94 (Abstract Only Provided).

Holden et al., "Quorum-sensing cross talk: isolation and chemical characterization of cyclic dipeptides from Pseudomonas aeruginosa and other Gram-negative bacteria," Moleclur Microbiology, 1999, vol. 33(6), pp. 1254-1266.

Hollyfield et al., "Oxidative damage-induced inflammation initiates age-related macular degeneration," Nature Medicine, 2008, vol. 14, No. 2, pp. 194-198.

Hong et al., "Inhibitory effect against Akt of cyclic dipeptides isolated from *Bacillus* sp" J. Microbiol. Biotechnol., 18, 682-685 (2008).

Houston et al., "The cyclic dipeptide Cl-4 [cyclo-(l-Arg-d-Pro)] inhibits family 18 chitinases by structural mimicry of a reaction intermediate," Biochem J., Nov. 15, 2002, vol. 368(Pt 1) (Abstract Only Provided).

Horwitz et al., "Piperazinedione plus total body irradiation: an alternative preparative regimen for allogeneic bone marrow transplantation in advanced phases of chronic myelogenous leukemia," Bone Marrow Transplantation, 1989, vol. 4, Iss. 1, pp. 101-105.

Hwang et al., "Effects of cyclo (his-pro) plus zinc on glucose metabolism in genetically diabetic obse mice," Diabetes Obes. Metab., Sep. 2003, vol. 5(5), pp. 317-324 (Abstract Only Provided).

Iriuchijima et al., "Thyrotripin-Releasing Hormone and Cyclo (His-Pro)-Like Immunoreactivities in the Cerebrospinal Fluids of 'Normal' Infants and Adults, and Patients with Various Neuropsychiatric and Neurologic Disorders," Life Sci. 1987, 41(22):2419-2428, Abstract only, from PubMed-PMID:2891013.

Ishibashi et al., "A Mechanism for Bitter Taste Sensibility in Peptides," Agric. Biol. Chem., 1988, vol. 52(3), pp. 819-827.

Ishibashi et al., "Bitterness of Leucine-Containing Peptides," Agric. Biol. Chem., 1987, vol. 51(9), pp. 2389-2394.

Ishii, et al. "Incidence of brain tumors in rats fed aspartame," Toxicology Letters, 1981, vol. 7, pp. 433-437.

Iyer et al. "Inflammatory lipid mediators in adipocyte function and obesity." Nature Reviews Endocrinology, Feb. 2010, vol. 6, pp. 71-82.

Jackson et al., "Amyotrophic Lateral Sclerosis: Thryrotropin-releasing hormone and histidyl proline diketopiperazine in the spinal cord and cerebrospinal fluid," Neurology, 1986, vol. 36(9), pp. 1218-1223.

Jamie et al., "The effect of the isomers of cyclo(Trp-Pro) on heart and ion-channel activity," J Pharm Pharmacol, Dec. 2002, vol. 54(12) (Abstract Only Provided).

Jara et al., "Elevated serum levels of cyclo (His-Pro), and endogenous inhibitor ofpituitary prolactin secretion, in systemic lupus erythematosus patients," Lupus, 1997, vol. 6(3) (Abstract Only Provided).

Jaspan et al., "Study of Passage of Peptides Across the Blood-Brain Barrier: Biological Effects of Cyclo(His-Pro) After Intravenous and Oral Administration," Annals of the New York Academy of Science, 1994, vol. 739, pp. 101-107 (Abstract Only Provided).

Jiang et al. "Asymmetric Reformastky reaction catalyzed by amino acid derivatives," Huaxue Tongbao CKNI, 2001, vol. 10, pp. 637-640 (English Abstract).

Jiang et al., "AKT signaling in regulating angiogenesis," Current Cancer Drug Targets, 2008, vol. 8, pp. 19-26.

Jicha et al., "Sequence Requirements for Formation of Conformational Variants of Tau Similar to Those Found in Alzheimer's Disease," Journal of Neuroscience Research, 1999, vol. 55, pp. 713-723.

Jones et al., "Enumeration and Phenotypic Characterization of Synovial Fluid Multipotential Mesenchymal Progenitor Cells in Inflammatory and Degenerative Arthritis," Arthritis & Rheumatology, 2004, vol. 50, Iss. 3, pp. 817-827.

Joosten et al., "IL-1αβ Blockade Prevents Cartilage and Bone Destruction in Murine Type II Collagen-Induced Arthritis, Whereas TNF-α Blockade Only Ameliorates Joint Inflammation," The Journal of Immunology, 1999, vol. 163, Iss. 9, pp. 5049-5055.

Jung et al., "Ex Vivo Expansion of Human Mesenchymal Stem Cells in Defined Serum-Free Media," Stem Cells International, 2012, Article ID 123030, 21 pages.

Kaakkola et al., "Effects of two diketopiperazines, cyclo (His-Pro) and cyclo (Asp-Phe), on striatal dopamine: A microdialysis study," Brain Research Bulletin, 1993, vol. 32(6), pp. 667-672.

Kanzaki et al., "Enzymatic synthesis of dehydro cyclo(His-Phe)s, analogs of the potent cell cycle inhibitor, dehydrophenylahistin, and their inhibitory activities toward cell division," Biosci Biotechnol Biochem, Nov. 2004, vol. 68(11), pp. 2341-2345 (Abstract Only Provided).

Kasperska-Zajac et al. "Platelet Activating Factor as a Mediator and Therapeutic Approach in Bronchial Asthma." Inflammation, Apr. 2008, vol. 31, No. 2, pp. 112-120.

Kikwai et al, "Stability and degradation profiles of Spantide II in aqueous solutions," Eur J Pharm Sci, Feb. 2006, vol. 27(2-3), pp. 158-166, Epub Nov. 2, 2005. (Abstract Only Provided).

Kilian et al., "Biological activity of selected tyrosine-containing 2,5-diketopiperazines," Pharmazie, Apr. 2005, vol. 60(4), pp. 305-309 (Abstract Only Provided).

Kilian et al., "The effect of the isomer of cyclo(Trp-Pro) on heart and ion-channel activity," J. Pharm. Pharmacol., Dec. 2002, vol. 54(12), pp. 1659-1665 (Abstract Only Provided).

Kobayashi et al., "Neuropeptide Y and histidyl-proline diketopiperazine," Rinsho-Kensa, Japan, Sep. 1987, vol. 21, No. 9, pp. 984-991.

Kopple et al. "Conformation of Cyclo-(l-Threonine)2 and Cyclo-(l-Allo Threonine)2 : A Proton and Carbon N.m.r. Study." International Journal of Peptide Protein Research, Jul. 1981, vol. 18, No. 1, pp. 33-40.

Koskinen, "Effect of Low Intravenous Doses of TRH, Acid-TRH and Cyclo (His-Pro) on Cerebral and Peripheral Blood Flows," British Journal of Pharmacology, 1986, vol. 87(3), pp. 509-519 (Abstract Only Provided).

Kow et al., "The Effects of the TRH Metabolite Cyclo(His-Pro) and Its Analogs on Feeding," Pharmacology, Biochemistry & Behavior, 1991, vol. 38, pp. 359-364.

Kuenz et al., "Plasma levels of soluble adhesion molecules sPECAM-1, sP-selectin and sE-selectin are associated with relapsing-remitting disease course of multiple sclerosis," J. Neuroimmunol, Oct. 2005, vol. 167(1-2), pp. 143-149.

Kulikov et al., "Review: The Bioregulatory Role of Platelet-Activating Factor in Intracellular Processes and Cell—Cell Interactions," 1997, www.protein.bio.msu.su/biokhimiya/contents/v63/full/63010057.html, pp. 1-13.

Kullenberg et al., "Intraarticular Corticosteroid Injection: Pain Relief in Osteoarthritis of the Hip?," Journal of Rheumatology, 2004, vol. 31, No. 11, pp. 2265-2268.

(56) References Cited

OTHER PUBLICATIONS

Kurahashi et al., "Histydyl-Proline Diketopiperazine (HPD), A Metabolite of Thyrotropin-Releasing Hormone (TRH), Improves the Ataxic Gait in 3-Acetylpyridine (3-AP) Treated Rats," No To Shinkei, Sep. 1986, vol. 38(9), pp. 893-898 (Abstract Only Provided).

Larsen et al. "Kinetics of degradation and oil solubility of ester prodrugs of a model dipeptide (Gly-Phe)," Eur J Pharm Sci, Aug. 2004, vol. 22(5), pp. 399-408 (Abstract Only Provided).

Lechan et al., "Thyrotropin Releasing Hormone but not Histidyl-Proline Diketopiperazine is Depleted from Rat Spinal Cord Following 5,7-Dihydroxytryptamine Treatment," Brain Research, 1985, vol. 326(1), pp. 152-155 (Abstract Only Provided).

Lechin et al., "Plasma Neurotransmitters and Cortisol in Chronic Illness: Role of Stress," J Medicine, 1994, vol. 25(3-4), pp. 181-192 (Abstract Only Provided).

Leduque et al., "Histidyl-Proline Diketopiperazine (His-Pro DKP) Immunoreactivity is Present in the Glucagon-Containing Cells of the Human Fetal Pancreas," J Clin Invest, 1987, 79(3):875-880 (Abstract Only Provided).

Lee et al., "Characterization of an Elastase Inhibitor Produced by Streptomyces lavendulae SMF11," Journal of Microbiology and Biotechnology, 2000, vol. 10, No. 1, pp. 81-85.

Lee et al., "Cyclo (Leu-Gly attenuates the striatal dopaminergic supersensitivity induced by chronic morphine," Alcohol Drugs Res, 1987, vol. 7(1) (Abstract Only Provided).

Lehninger et al., "Amino Acids and Peptides," Chapter 5 of Principles of Biochemistry, 1993, 2nd edition, pp. 111-133.

Lewis et al., "Hydrogen Peroxide Stimulates the Synthesis of Platelet-activating Factor by Endothelium and Induces Endothelial Cell-dependent Neutrophil Adhesion," The Journal of Clinical Investigation, 1988, vol. 82, Iss. 6, pp. 2045-2055.

Lindsley et al., "Allosteric Akt (PKB) inhibitors: discovery and SAR of isozyme selective inhibitors," Bioorganic & Medicinal Chemistry Letters, 2005, vol. 15, Iss. 3, pp. 761-764.

Lindner et al., "[Effects of cyclic adenosine-3',5'-monophosphate and cyclo{Lys-Pro}.HCl neuronotrophic factors in tissue culture]," J Hirnforsch, 1987, vol. 28(3) (Abstract Only Provided).

Liu et al., "Hydroxyprolylserine derivatives JBP923 and JBP485 exhibit the antihepatitis activities after gastrointestinal absorption in rats," J Pharmacol Exp Ther, Aug. 2000, vol. 294(2) (Abstract Only Provided).

Luca et al., "Determination of serotonin content and ceruloplasmin activity, of blood and CSF amino acid level in multiple sclerosis," Neurol Psychiatr (Bucur), 1986, vol. 24(3), pp. 153-159.

Lucietto et al., "The biological activity of the histidine-containing diketopiperazines cyclo (His-Ala) and cyclo (His-Gly)," Peptides, Nov. 2006, vol. 27(11), pp. 2706-2714, Epub Jun. 21, 2006 (Abstract Only Provided).

Lupia et al., "Role of tumor necrosis factor-α and platelet-activating factor in neoangiogenesis induced by synovial fluids of patients with rheumatoid arthritis," European Journal of Immunology, 1996, vol. 26, Iss. 8, pp. 1690-1694.

Ma et al., "Platelet-Activating Factor (PAF) Induces Corneal Neovascularization and Upregulates VEGF Expression in Endothelial Cells," Investigative Ophthalmology & Visual Science, 2004, vol. 45, No. 9, pp. 2915-2921.

Matejschuk et al., "Production of human albumin solution: a continually developing colloid," British Journal of Anaesthesia, 2000, vol. 85, Iss. 6, pp. 887-895.

Mayer, "Immunology—Chapter Four," Immunoglobulins—Structure and Function, online at pathmicro.med.sc.edu/mayer/IgStruct2000.htm, University of South Carolina School of Medicine, Nov. 6, 2009, 8 pages.

Mazza et al., "Potential energy calculations on phenylalanine rotamers in different boat forms of proline-containing cyclic dipeptides," Int. J. Pept. Protein Res., vol. 31, Feb. 1988, pp. 157-163.

McCain et al., "Endorphinergic modulation of immune function: potent action of the dipeptide glycyl-L-glutamine," Life Science, 1987, vol. 41, pp. 169-176.

McCain et al., "Modulation of Human T-Cell Suppressor Activity by Beta Endorphin and Glycyl-L-Glutamine," Int. J. Immunopharmoc, 1986, vol. 8(4), pp. 443-446.

McCleland et al., "An investigation into the biological activity of the selected histidine-containing diketopieperazines cyclo(His-Phe) and cyclo(His-Tyr)," Journal of Pharmacy and Pharmacology, Sep. 2004, vol. 56(9), pp. 1143-1153.

Meester et al., "In Vivo Inhibition of Dipeptidyl Peptidase IV Activity by Pro-Pro-diphenyl-phosphonate (Prodipine)," Biochemical Pharmacology, 1997, vol. 54, pp. 173-179.

Meltzer, "Efficacy and patient satisfaction with cromolyn sodium nasal solution in the treatment of seasonal allergic rhinitis: a placebo-controlled study," Clinical Therapeutics, 2002, vol. 24, Iss. 6, pp. 942-952.

Mentlein et al., "Dipeptidyl-Peptidase IV Hydrolyses Gastric Inhibitory Polypeptide, Glucagon-Like Peptide-1 (7-36)amide, Peptide Histidine Methionine and is Responsible for their Degradation in Human Serum," European Journal of Biochemistry, 1993, vol. 214(3), pp. 829-835 (Abstract Only Provided).

Mesh, "Autoimmune Diseases," internet document www.ncbi.nlm.nih.gov/sites/entrez, accessed Oct. 31, 2007, 2 pages.

Michell et al., "Biomarkers and Parkinson's Disease," Brain, Aug. 2004, vol. 127, pp. 1693-1705.

Miller et al., "Peptide Inhibitor of Interleukin-8 (IL-8) Reduces *Staphylococcal* Enterotoxin-A (SEA) Induced Neutrophil Trafficking to the Lung," Inflamm. Res., 1996, vol. 45, pp. 393-397.

Milne, et al. "The biological activity of selected cyclic dipeptides," J. Pharm. Pharmacol., 1998, vol. 50, pp. 1331-1337.

Minelli et al., "Phosphoproteomic analysis of the effect of cyclo-[His-Pro] dipeptide on PC12 cells." Peptides, Jan. 2006;27(1):105-13. Epub Aug. 30, 2005., Abstract only PMID: 16137790.

Mitsuma et al., "Radioimmunoassay for Thyrotropin-Releasing Hormone Precursor Peptide, Lys-Arg-Gln-His-Pro-Gly-Arg-Arg," Exp Clin Endocrinology, 1989, vol. 93(1), pp. 53-60 (Abstract Only Provided).

Mizuma et al., "Concentration-Dependent Preferences of Absorptive and Excretive Transport Cause Atypical Intestinal Absorption of Cyclic Phenylalanylserine: Small Intestine Acts as an Interface Between the Body and Ingested Compounds," Research Communications in Molecular Pathology and Pharmacology, 2002, vol. 111, pp. 199-209.

Mizuma et al., "Intestinal Absorption of Stable Cyclic Glycylphenylalanine: Comparison with the Linear Form," J. Pharm. Pharmacol., 1997, vol. 49, pp. 1067-1071.

Molodavkin et al., "[Effect of the novel dipeptide nootropic agent noopept and its metabolite cyclo-L-prolylglycine on the transcallosal evoked potential in the rat brain]," Eksp Klin Farmakol, Mar.-Apr. 2002, vol. 65(2) (Abstract Only Provided).

Monaco et al., "Plasma and cerebrospinal fluid tryptophan in Multiple Sclerosis and Degenerative Diseases," J Neurol Neurosurg Psychiatry, 1979, vol. 42(7), pp. 640-641 (Abstract Only Provided).

Montine et al., "Cerebrospinal Fluid Ab42, Tau, and F2-Isoprostane Concentrations in Patients with Alzheimer Disease, Other Dementias, and in Age-Matched Controls," Acrch Pathol Lab. Med, Apr. 2001, vol. 125, pp. 510-512.

Mori et al., "Alteration by Liquid Protein Diet of TRH and Cyclo(His-Pro) in the Young Rat Brain," Res. Commun Chem Pathol Pharmacol, 1985, vol. 47(1), pp. 157-160 (Abstract Only Provided).

Mori et al., "Brain TRH and Cyclo (His-Pro) and Brain Protein in the Newborn Rat are Altered by Maternal Liquid Protein Feeding," Life Sci, 1983, vol. 32(14), pp. 1607-1612 (Abstract Only Provided).

Mori et al., "Distribution of histidyl-proline diketopiperazine [cyclo (His-Pro)] and thyrotropin-releasing hormone (TRH) in the primate central nervous system," Brain Res, 1982, vol. 245(1), pp. 183-186.

Mori et al., "Histidyl-Proline Diketopiperazine Cyclo (His-Pro): Identification and Characterization in Rat Pancreatic Islets," Biochem Biophys Res Commun, 1983, vol. 115(1), pp. 281-286 (Abstract Only Provided).

Mori et al., "Histidyl-Proline Diketopiperazine cyclo (His-Pro): measurement by radioimmunoassay in human blood in normal subject and in patients with hyper-and hypothyroidism," Biochem Biophys Res Commun, 1982, vol. 109(2), pp. 541-547.

(56) References Cited

OTHER PUBLICATIONS

Mori et al., "Regional Dissociation of Histidyl-Proline Diketopiperazine (Cyclo-(His-Pro)) and Thyrotropin-Releasing Hormone (TRH) in the Rat Brain," Brain Research, 1982, vol. 231(2), pp. 451-453 (Abstract Only Provided).
Mori et al., "Specific Radioimmunoassay of Cyclo (His-Pro), a Biologically Active Metabolite of Thyrotropin-Releasing Hormone," Endocrinology, 1981, vol. 108(5), pp. 1995-1997 (Abstract Only Provided).
Mori et al., ["TRH and Cyclo (His-Pro) Concentrations in the Young Rat Brain are Altered by a Liquid Protein Diet]," [Article in Japanese], Nippon Naibunpi Gakkai Zasshi, 1987, vol. 63(7), pp. 846-852 (English Abstract Only).
Morley et al., "Histidyl-proline diketopiperazine decreases food intake in rats," Brain Research, 1981, vol. 210, Iss. 1-2, pp. 475-478.
Morley et al., "Neuropeptides and appetite: contribution of neuropharmacological modeling," Fed. Proc., Nov. 1984, vol. 43(14), pp. 2903-2907 (Abstract Only Provided).
Moss et al. "Th1/Th2 cells in inflammatory disease states: therapeutic implications," Expert Opinion on Biological Therapy, Dec. 2004, vol. 4, No. 12, pp. 1887-1896.
Moss et al., "Kinetics and Mechanism of the Facile Cyclization of Histidyl-Prolineamide to Cyclo (His-Pro) in Aqueous Solution and the Competitive Influence of Human Plasma," J Pharm Pharmacol, 1990, vol. 42(1), pp. 7-12 (Abstract Only Provided).
Murray et al., "Role of α-Synuclein Carboxy-Terminus on Fibril Formation in Vitro," Biochemistry, 2003, vol. 42, pp. 8530-8540.
Nakamura et al., "T-cell mediated inflammatory pathway in osteoarthritis," Osteoarthritis & Cartilage, 1999, vol. 7, pp. 401-402.
Neustadt, "Intra-articular injections for osteoarthritis of the knee," Cleveland Clinic J. Med., 2006, vol. 73(10), pp. 897-911.
Nicholson et al., "NPI-2358 is a tubulin-depolymerizing agent: in-vitro evidence for activity as a tumor vascular-disrupting agent," Anticancer Drugs, Jan. 2006, vol. 17(1), pp. 25-31 (Abstract Only Provided).
Nicolson, "Metabolic syndrome and mitochondrial function: Molecular replacement and antioxidant supplements to prevent membrane peroxidation and restore mitochondrial function," Journal of Cellular Biochemistry, 2007, vol. 100, Iss. 6, pp. 1352-1369.
Nitecki et al., "A Simple Route to Sterically Pure Kiketopiperazines" J. Org. Chem., 1968, vol. 33(2), pp. 864-866.
O'Connor et al., "Post-proline dipeptidyl-aminopeptidase from synaptosomal membranes of guinea-pig brain," European Journal of Biochemistry, 1986, vol. 154, Iss. 2, pp. 329-335.
Ostrovskaia et al., "Multicomponent antithrombotic effect of the neuroprotective prolyl dipeptide GVS-111 and its major metabolite cyclo-L-prolylglycine," Eksp Klin Farmakol, Mar.-Apr. 2002, vol. 65(2) (Abstract Only Provided).
Otani et al., "Bone marrow-derived stem cells target retinal astrocytes and can promote or inhibit retinal angiogenesis," Nature Medicine, 2002, vol. 8, No. 9, pp. 1004-1010.
Oztuna et al., "Intra-articular Injection of Tenoxicam in Osteoarthritic Knee Joints With Effusion," Orthopedics, 2007, vol. 30, Iss. 12, pp. 1039-1042.
Palace et al. "Epilepsy: an autoimmune disease?" Journal of Neurology, Neurosurgery & Psychiatry, Dec. 2000, vol. 69, No. 6, pp. 711-714.
Palacios et al., "Tenidap Decreases IL-8 and Monocyte Chemotactic Peptide-1 (MCP-1) mRNA Expression in the Synovial Tissue of Rabbits with Antigen Arthritis and in Cultured Synovial Cells," Clin. Exp. Immunol., 1998, vol. 111, pp. 588-596.
Pandey et al., "Synthetic Peptides Corresponding to a Repetitive Sequence of Malarial Histidine Rich Protein Bind Haem and Inhibit Haemozoin Formation in vitro," Mol Biochem Parasitol, 1997, vol. 90(1), pp. 281-287 (Abstract Only Provided).
Parker et al., "Evidence for the Presence of Immunoreactive Histidyl-Proline Diketopiperazine [Cyclo (His-Pro)] in the Adult Human Brain," Peptides, Nov.-Dec. 1983, vol. 4(6), pp. 879-881 (Abstract Only Provided).

Pötgens et al., "Covalent dimerization of vascular permeability factor/vascular endothelial growth factor is essential for its biological activity. Evidence from Cys to Ser mutations," The Journal of Biological Chemistry, 1994, vol. 269, Iss. 52, pp. 32879-32885.
Pekary et al., "In vitro Production of a TRH-Homologous Peptide and His-Pro Diketopiperazine by Human Semen," J Androl, 1985, vol. 6(6), pp. 379-385 (Abstract Only Provided).
Potocka et al., "Pharmacokinetic characterization of the novel pulmonary delivery excipient fumaryl diketopiperazine," J. Diabetes Sci. Technol., Sep. 2010, vol. 4(5), pp. 1164-1173 (Abstract Only Provided).
Pountos et al., "NSAIDS inhibit in vitro MSC chondrogenesis but not osteogenesis: implications for mechanism of bone formation inhibition in man," Journal of Cellular and Molecular Medicine, 2011, vol. 15, Iss. 3, pp. 525-534.
Prakash et al., "Synthesis and Biological Activity of Novel Neuroprotective Diketopiperazines," Bioorganic & Medicinal Chemistry, Sep. 2002, vol. 10(9), pp. 3043-3048.
Prasad et al., "Distribution and Characterization of Cyclo (His-Pro)-Like Immunoreactivity in Human Cerebrospinal Fluid," Biochem Biophys Res Commun, 1986, vol. 136(2), pp. 835-842 (Abstract Only Provided).
Prasad et al., "Distribution and Metabolism of Cyclo (His-Pro): A New Member of the Neuropeptide Family," Peptides, May-Jun. 1982, vol. 3(3), pp. 591-598 (Abstract Only Provided).
Prasad et al., "Increased cerebrospinal fluid cyclo(His-Pro) content in schizophrenia," Neuropeptides, Nov. 1991, vol. 20(3), pp. 187-190.
Prasad et al., "Isolation of cyclo(His-Pro)-like immunoreactivity from Human Urine and Demonstration of its Immunologic, Pharmacologic, and Physico-chemical Identity with the Synthetic Peptide," Biochemistry Int, 1990, vol. 21(3), pp. 425-434 (Abstract Only Provided).
Prasad et al., "Thermoregulation in rats: opposing effects of thyrotropin releasing hormone and its metabolite histidyl-proline diketopiperazine," Biochem Biophys Res. Commun., 1978, vol. 85(4), pp. 1582-1587.
Prasad, "Bioactive Cyclic Dipeptides," Peptides, 1995, vol. 16(1), pp. 151-164.
Purves et al. (Eds), Neuroscience, 2001, Sinauer Associates, Inc., 2nd Edition, pp. 75, 367, 400 and 403.
Purves et al., Life: the Science of Biology, 3rd Ed. (1992), p. 376.
Rabago et al, "Prolotherapy: An Effective Adjunctive Therapy for Knee Osteoarthritis," The Journal of the American Osteopathic Association, 2013, vol. 113, Iss. 2, pp. 122-123.
Rainbow et al., "Distribution, survival and biological effects in mice of a behaviorally active, enzymatically stable peptide: pharmacokinetics of cyclo(Leu-Gly) and puromycin-induced amnesia," Pharmacol Biochem Behav, May 1979, vol. 10(5), pp. 787-793.
Rainger et al., "Endothelial-Borne Platelet-Activating Factor and Interleukin-8 Rapidly Immobilize Rolling Neutrophils," Am. J. Physiol., 272(Heart Circ. Physiol. 41):H114-H122 (1997).
Rainsford et al., "Effects of 5-Lipoxygenase Inhibitors on Interleukin Production by Human Synovial Tissues in Organ Culture: Comparison with Interleukin-1-Synthesis Inhibitors," J. Pharm. Pharmacol., 48:46-52 (1996).
Ramírez et al., "Platelet Activating Factor Modulates Microvascular Permeability through Nitric Oxide Synthesis," Microvascular Research, 1995, vol. 50, Iss. 2, pp. 223-234.
Reubsaet et al., "Qualitative and Quantitative Aspects of the Degradation of Several Tripeptides Derived from the Antitumor Peptide Antagonist [Arg(6), D-Trp(7,9), MePhe(8)] Substance P[6-11]," J Pharm Biomed Anal 1999, 19(3-4):2.
Rinaldi et al. "Immunological markers in multiple sclerosis: tackling the missing elements," Neurol. Sci., Dec. 2005, vol. 26 Suppl. 4, pp. S215-S217.
Rosenthal et al., "Effects of Arachidonic Acid and Cyclo (His-Pro) on Zinc Transport Across Small Intestine and Muscle Tissues," Life Sei, 2001, vol. 70(3), pp. 337-348 (Abstract Only Provided).
Roth et al., "Platelet-Activating Factor Exerts Mitogenic Activity and Stimulates Expression of Interleukin 6 and Interleukin 8 in Human Lung Fibroblasts via Binding to its Functional Receptor," J. Exp. Med., 1996, vol. 184, pp. 191-201.

(56) References Cited

OTHER PUBLICATIONS

Rozga et al., "Human albumin: old, new, and emerging applications," Annals of Transplantation, 2013, vol. 18, pp. 205-217.
Saha et al., "Interleukin-1β—converting enzyme/caspase-1 in human osteoarthritic tissues: Localization and role in the maturation of interleukin-1β and interleukin-18," Arthritis & Rheumatology, 1999, vol. 42, Iss. 8, pp. 1577-1587.
Sakkas et al., "T Cells and T-Cell Cytokine Transcripts in the Synovial Membrane in Patients with Osteoarthritis", Clinical and Diagnostic Laboratory Immunology, Jul. 1998, vol. 5, No. 4, pp. 430-437.
Sakurada et al., "Antinociceptive activities of synthetic dipeptides in mice." J. Pharm. Pharmacol., 1982, vol. 34, pp. 750-751.
Sakuta et al., "Dual Regulatory Effects of Interferon-α, -β, and -γ on Interleukin-8 Gene Expression by Human Gingival Fibroblasts in Culture Upon Stimulation with Lipopolysaccharide from Prevotella Intermedia, Interleukin-1α, or Tumor Necrosis Factor-α," J. Dent Res., 1998, vol. 77(8), pp. 1597-1605.
Samanta et al., "Crystal Structure of Human Plasma Platelet-activating Factor Acetylhydrolase," J. Biol. Chem., vol. 283(46), Nov. 14, 2008, pp. 31617-31624.
Sammes, "Naturally Occurring 2,5-Dioxopiperazines and Related Compounds," Fortschr. Chem. Org. Naturst., 1975, vol. 32, pp. 51-118.
Sano et al. "Process Research and Development of L-Alanyl-L-Glutamine, a Component of Parenteral Nutrition," Organic Process Research & Development, 2000, vol. 4, pp. 147-152.
Sato et al., "Comparison of the antiociceptive effect between the cyclic dipeptide cyclo[Tyr(Et)-homoarginine] and the linear dipeptide Boc-Tyr(Et)-homoarginine-Ome in rats.," Jpn J Pharmacol, Jan. 1984, vol. 34(1) (Abstract Only Provided).
Scharpe et al., "Peptide Truncation by Dipeptidyl Peptidase IV: A New Pathway for Drug Discovery," Verh K. Acad Geneeskd Belg. 2001, vol. 63(1), pp. 5-32 (Abstract Only Provided).
Schlingemann et al., "Role of vascular permeability factor/vascular endothelial growth factor in eye disease," Brit. J. Ophthalmology, vol. 81, 1997, pp. 501-512.
Sepetov et al., "Rearrangement, Racemization and Decomposition of Peptides in Aqueous Solution," Peptide Research, 1991, vol. 4(5), pp. 308-313 (Abstract Only Provided).
Seredenin et al. "Endogenous dipeptide cycloprolylglycine shows selective anxiolytic activity in animals with manifest fear reaction," Bull Exp Biol Med; Apr. 2002; vol. 1333(4) (Abstract Only Provided).
Shaw et al., "Future of early detection of lung cancer: the role of mouse models." Clin Cancer Res., Jul. 1; 11(13 Pt 2): 4999s-5003s, 2005.
Shimazaki et al., "Diketopiperazine Derivatives, a New Series of Platelet-Activating Factor Inhibitors," Chem. Pharm. Bull., 1987, vol. 35(8), pp. 3527-3530.
Shimazaki et al., "Diketopiperazines as a New Class of Platelet-Activating Factor Inhibitors," J. Med. Chem., 1987, vol. 30, pp. 1706-1709.
Shimazaki et al., "PAF Inhibitory Activity of Diketopiperazines: Structure-Activity Relationships," Lipids, 1991, vol. 26(12), pp. 1175-1178.
Shimi et al., "Isolation of Cairomycins A and C," Antimicrobial Agents and Chemotherapy, Jun. 1981, vol. 19(6), pp. 941-944.
Shimonkevitz et al., "A Diketopiperazine Fragment of Human Serum Albumin Modulates T-Lymphocyte Cytokine Production Through Rap1," Journal of Trauma, Injury, Infection, and Critical Care, 2008, vol. 64, No. 1, pp. 35-41.
Shukla et al., "Role of Endogenous Cyclo(His-Pro) in Cold-Induced Hypothermia in the Desert Rat (Mastomys Natalensis)," Peptides; 1994; 15(8):1471-4 (Abstract Only Provided).
Shutov et al., "[Diagnostic Significance of the type of In Vitro Interaction between Blood Lymphocytes and Serotonin in Multiple Sclerosis]," [Article in Russian], Zh Nevrol Psikhiatr Im S S Korsakova, 2002, vol. 102(4), pp. 35-38 (Abstract Only Provided).

Skates et al., "Molecular markers for early detection of renal carcinoma: investigative approach," Clin Cancer Res, Sep. 2004, vol. 10(18 Pt 2), pp. 6296S-6301S.
Slater, "Gas-liquid chromatography of 2,5-diketopiperazines as their trifluoroacetyl derivatives," Journal of Chromatography A, 1972, vol. 64, Iss. 1, pp. 166-169.
Smith et al., "Lesson 10, vol. 12—Asthma: Evolving Anti-Inflammatory Therapy," www.chestnet.org/education/pccu/vol12/lesson10.html, pp. 1-8, printed Jul. 20, 2000.
Smith et al., "Recent developments in drug therapy for multiple sclerosis," Mult. Scler., 1999, vol. 5, pp. 110-120.
Smith et al., "Solid-phase synthesis of a library of piperazinediones and diazepinediones via Kaiser oxime resin." Bioorg. Med. Chem., 1998, vol. 8, pp. 2369-2374.
Sohn et al. "Plasma proteins present in osteoarthritic synovial fluid can stimulate cytokine production via Toll-like receptor 4," Arthritis Research & Therapy, 2012, vol. 14, R7, 13 pages.
Sollid et al. "Is celiac disease an autoimmune disorder?" Current Opinion in Immunology, Dec. 2005, vol. 17, No. 6, pp. 595-600.
Sollis "Short and novel stereospecific synthesis of trisubstituted 2,5-diketopiperazines," J Org Chem, Jun. 2005, vol. 70(12), pp. 4735-4740 (Abstract Only Provided).
Song et al., "Body weight reduction in rats by oral treatment with zinc plus cyclo-(His-Pro)," Br. J. Pharmacol., Sep. 2009, vol. 158(2), pp. 442-450, Epub May 5, 2009 (Abstract Only Provided).
Song et al., "Raw vegetable food containing high cyclo (his-pro) improved insulin sensitivity and body weight control," Metabolism, Nov. 2005, vol. 54(11), pp. 1480-1489 (Abstract Only Provided).
Song et al., "Synergistic Antidiabetic Activities of Zinc, Cyclo (His-Pro), and Arachidonic Acid," Metabolism 2001 50(1):53-59 (Abstract Only Provided).
Stark et al., "Structures, sensory activity, and dose/response functions of 2,5-diketopiperazines in roasted cocoa nibs (Theobroma cacao)." J Agric Food Chem., Sep. 7, 2005, vol. 53(18), pp. 7222-7231 (Abstract Only Provided) PMID: 16131134.
Steiner et al., "Histidyl Proline Diketopiperazine (Cyclo [His-Pro]) in Eating Disorders," Neuropeptides, Oct. 1989, vol. 14(3), pp. 185-189 (Abstract Only Provided).
Strom et al., "Lactobacillus plantarum MiLAB 393 produces the antifungal cyclic dipeptides cyclo(L-Phe-L-Pro) and cyclo(L-Phe-trans-4-OH-L-Pro) and 3-phenyllactic acid.," Appl Environ Microbiol, Sep. 2002, vol. 68(9) (Abstract Only Provided).
Suguna et al., "Crystal structures of diketopiperazines containing α-aminoisobutyric acid: Cyclo(Aib-Aib) and cyclo(Aib-L-lle)," Biopolymers, 1982, vol. 21, Iss. 9, pp. 1847-1855.
Suzuki et al., "Effect of cyclic dipeptides containing histidine on pentobarbital narcosis," J. Pharm. Dyn., May 1981, vol. 4(5), pp. 377-379.
't Hart et al., "Evaluating the validity of animal models for research into therapies for immune-based disorders," DDT, 2004, vol. 9(12), pp. 517-524.
Takahara et al., "Detection in Human Serum by Radioimmunoassay of Histidyl-Proline Diketopiperazine, a Metabolite of Thyrotropin-Releasing Hormone," J Clinical Endocrinology, 1983, vol. 56(2), pp. 312-319 (Abstract Only Provided).
Tascioglu et al., "Efficacy of intra-articular sodium hyaluronate in the treatment of knee osteoarthritis," Clinical Rheumatology, 2003, vol. 22, Iss. 2, pp. 112-117.
Teitel et al., "Rheumatoid arthritis," PubMed Health, reviewed Feb. 2, 2012, available at www.ncbi.nlm.nih.gov/pubmedhealth/PMH0001467/?report=printable, 8 pages.
Teitel et al., "Scleroderma," PubMed Health, reviewed Feb. 2, 2012, available at www.ncbi.nlm.nih.gov/pubmedhealth/PMH0001465/?report=printable, 7 pages.
Teitel et al., "Systemic lupus erythematosus," PubMed Health, reviewed Feb. 2, 2012, available at www.ncbi.nlm.nih.gov/pubmedhealth/PMH0001471/?report=printable, 9 pages.
Thomas et al. "Anti-Inflammatory Activity in the Low Molecular Weight Fraction of Commercial Human Serum Albumin (LMWF5A)," Journal of Immunoassay and Immunochemistry, 2016, vol. 37, Iss. 1, pp. 55-67.

(56) References Cited

OTHER PUBLICATIONS

Unal et al., "Cyclo(Gly-Gln) inhibits the cardiorespiratory depression produced by beta-endorphin and morphine," Brain Research, 1997, vol. 747(1), pp. 52-59.
Vara et al., "PI3K/Akt signalling pathway and cancer," Cancer Treatment Reviews, 2004, vol. 30, pp. 193-204.
Varughese et al., "Crystal structure and conformation of cyclo-L-cystine," Int. J. Pept. Protein Res., vol. 18, Jul. 1981, pp. 88-102.
Vogel et al., "Dissiminated tumor cells—Their detection and significance for prognosis of gastrointestinal and pancreatic carcinomas," Virchows Arch, 2001, vol. 439, pp. 109-117.
Walter et al., "Neurohypophyseal hormones, analogs, and fragments: their effect on puromycin-induced amnesia," Proc. Natl. Acad. Sci., Oct. 1975, vol. 72(10), pp. 4180-4184.
Walter et al., "The Cyclized C-Terminal Dipeptide of Arginine Vasopressin: Metabolic Stability and Antagonism of Puromycin-induced Amnesia," Hormones and Behavior, 1982, vol. 16; p. 234-244.
Wang et al., "A facile pathway to synthesize diketopiperazine derivatives," Tetrahedron Lett, 2002, vol. 43, pp. 865-867.
Wang et al., "Novel inhibitors of plasminogen activator inhibitor-1: development of new templates from diketopiperazines," Bioorg Med Chem Lett, Sep. 2002, vol. 12(17), pp. 2367-2370 (Abstract Only Provided).
Watterson et al., "Viscosupplementation: Therapeutic Mechanisms and Clinical Potential in Osteoarthritis of the Knee," Journal of the American Academy of Orthopaedic Surgeons, 2000, vol. 8, No. 5, pp. 277-284. Abstract Only.
Weng et al., "Novel CCK-B receptor agonists: diketopiperazine analogues derived for CCK4 bioactive conformation," Regul Pept, Aug. 1996; vol. 65(1) (Abstract Only Provided).
Wennemers et al., "Diketopiperazine Receptors: A Novel Class of Highly Selective Receptors for Binding Small Peptides," Chem. Eur. J., 2001, vol. 7, No. 15, pp. 3342-3347.
Weszl et al., "Freeze-Dried Human Serum Albumin Improves the Adherence and Proliferation of Mesenchymal Stem Cells on Mineralized Human Bone Allografts," Journal of Orthopaedic Research, 2012, vol. 30, Iss. 3, pp. 489-496.
Wilber et al., "Endogenous histidyl-proline diketopiperazine [cyclo (His-Pro)]: a potential satiety neuropeptide in normal and genetically obese rodents," Trans Assoc Am Physicians, 1983, vol. 96, pp. 131-136.
Wilber et al., "Histidyl-proline diketopiperazine: a potent and chronic appetite-inhibiting neuropeptide," Trans Assoc. Am Physicians, 1986, vol. 99, pp. 245-249.
Wilkes et al. "Patient Survival after Human Albumin Administration: A Meta-Analysis of Randomized, Controlled Trials." Annals of Internal Medicine, Aug. 2001, vol. 135, No. 3, pp. 149-164.
Wisniewski et al., "Relationship between serum cyclo (His-Pro) concentrations and the nutritional status of HIV-infected patients," South Med. J., Mar. 1994, vol. 87(3), pp. 348-351 (Abstract Only Provided).
Woehlecke et al., "Reversal of breast cancer resistance protein-mediated drug resistance by tryprostatin A.," Int J Cancer; Dec. 2003, vol. 107(5) (Abstract Only Provided).
Wolf et al., "Identification of Cyclo(His-Pro)-Like Immunoreactivity in Human Follicular Fluid: Correlation with Steroid and Peptide Hormones," J Soc Gynecol Investigation, 1994, vol. 1 (3), pp. 220-224 (Abstract Only Provided).
Wretlind, "The Availability of the Isopropyl Ester of L-and D-Phenylalanine and 3,6-Dibenzyl-2,5-Diketopiperazine form Growth in Rats," Acta phys. Scandinav, May 1953, vol. 30, pp. 97-104.
Wyatt et al., "2,5-Diketopiperazines as potent and selective oxytocin antagonists 1: Identification, stereochemistry and initial SAR," Bioorg Med Chem Lett., May 16, 2005, vol. 15(10), pp. 2579-2582 (Abstract Only Provided) PMID: 15863320.
Yamada et al., "Abundance of Cyclo (His-Pro)-like Immunoreactivity in the Brain of TRH-Deficient Mice," Endocrinology, Jan. 1999, vol. 140(1), pp. 538-541 (Abstract Only Provided).
Yanagisawa et al., "The Subcellularand Organ Distribution and Natural Form of Histidyl-Proline Diketopiperazine in Rat Brain Determined by a Specific Radioimmunoassay," J Biol Chem, Nov. 10, 1980, vol. 255(21), pp. 10290-10294 (Abstract Only Provided).
Yang et al., "Increased hepatic platelet activating factor (PAF) and PAF receptors in carbon tetrachloride induced liver cirrhosis." Gut, Jan. 2004, vol. 53, No. 6, pp. 877-883.
Yasukawa, "Inflammation in age-related macular degeneration: pathological or physiological?", Expert Review of Ophthalmology, 2009, vol. 4, Iss. 2, pp. 107-112.
Yi Es, "Hypersensitivity pneumonitis," Crit Rev Clin Lab Sci., Nov. 2002, vol. 39(6), pp. 581-629.
Yoshida et al., "PAF Inhibitors of Microbial Origin," Prog. Biochem. Pharmacol., 1988, vol. 22, pp. 68-80.
Youngblood et al., "Bovine Serum Albumin-GABA-His-Pro-NH2: an Immunogen for Production of Higher Affinity Antisera for TRH," J Neursci Methods, 1983, vol. 9(4), pp. 367-373 (Abstract Only Provided).
Zander et al., "Allogeneic bone marrow transplantation for acute leukemia refractory to induction chemotherapy," Cancer, 1985, vol. 56, Iss. 6, pp. 1374-1379.
Zeng et al., "Synthesis of a small library of diketopiperazines as potential inhibitors of calpain," Bioorg Med Chem Lett, Jun. 2005, vol. 15(12), pp. 3034-3038.
Zhang et al., "Inhibition of the prostaglandin-degrading enzyme 15-PGDH potentiates tissue regeneration," Science, 2015, vol. 348, No. 6240, pp. 2340-1-2340-8.
Zieve, "Multiple sclerosis," PubMed Health, reviewed Sep. 26, 2011, available at www.ncbi.nlm.nih.gov/pubmedhealth/PMH0001747/?report=printable, 10 pages.
Ziong et al., "Chemical Constituents from Phytolacca polyandra" Yunnan Zhiwu Yanjiu, 2002, vol. 24, No. 3, pp. 401-405. (English abstract).
International Search Report and Written Opinion for International (PCT) Patent Application No. PCT/US16/38774 dated Sep. 14, 2016, 13 pages.
International Preliminary Report on Patentability for International (PCT) Patent Application No. PCT/US16/38774 dated Jan. 4, 2018, 12 pages.
"AP-007 Study to Evaluate Safety and Exploratory Efficacy of Three Intra-articular Injections of Ampion in the Knee of Adults With Pain Due to Osteoarthritis," U.S. National Library of Medicine, 2016 [retrieved on May 16, 2018], 7 pages. Retrieved from: clinicaltrials.gov/ct2/history/NCT02184156?V_2=View#StudyPageTop.
Millett et al., "Shoulder Osteoarthritis: Diagnosis and Management", American Family Physician, 2008, vol. 78, Iss. 5, pp. 605-611.
Extended European Search Report for European Patent Application No. 16815219.7 dated Jan. 18, 2019, 9 pages.
Official Action for European Patent Application No. 16815219.7 dated Apr. 9, 2020, 8 pages.

\* cited by examiner

USE OF LOW MOLECULAR WEIGHT FRACTIONS OF HUMAN SERUM ALBUMIN IN TREATING DISEASES

CROSS-REFERENCE TO RELATED APPLICATIONS

This application claims the benefit of priority under 35 U.S.C. § 119(e) to U.S. Provisional Patent Application No. 62/182,985, filed Jun. 22, 2015 and U.S. Provisional Patent Application No. 62/318,873, filed Apr. 4, 2016. The entire disclosure of U.S. Provisional Patent Application No. 62/182,985 and U.S. Provisional Patent Application No. 62/318,873 are incorporated herein by reference.

FIELD OF THE INVENTION

This invention relates to the treatment of diseases using a low molecular weight fraction (LMWF) of human serum albumin (HSA) wherein at least one of its components comprises a diketopiperazine (DKP) having amino acid side chains of alanine and aspartic acid and referred to as DA-DKP. In particular, the present invention teaches the use of this LMWF of HSA to modulate various aspects of the immune system such as, for example, inflammation, T-cells and various cytokines.

BACKGROUND

The vertebrate immune system is comprised of subsystems that are classified depending on the type of immune response being mounted. These subsystems work together to mount an initial immune response following an infection or damage and to produce a more specific response to the infecting organism over time. For example, one such subsystem is the innate immune system (also referred to as the non-specific immune system). The innate immune system often referred to as the first line of defense because molecules and cells of the innate immune system mount a generic response to threats to the individual. That is, the innate immune system responds similarly to all damage and infections without regard to the specificity of the damaging or infectious agent. Inflammation is one of the first parts of the innate immunes system to respond to an insult. Inflammation is mediated by numerous chemical agents released by damaged or infected cells and serves to produce a physical barrier to further infection and also helps promote healing of damaged tissue. Examples of such agents include platelet activating growth factor (PAGF), which is a potent activator and mediator of inflammation, and interleukin-8 (IL-8; neutrophil chemotactic factor), which induces migration of primary neutrophils to sites of infection and initiation of phagocytosis.

A second subsystem of the immune system is the adaptive immune system (acquired immune system, specific immune system). The adaptive immune system is comprised of immune molecules (e.g., cytokines) and highly specialized immune cells that evolve to recognize specific molecules from specific pathogens. Examples of cells that make up the adaptive immune system include T and B-cells.

T-cell mediated diseases represent a large number of immune system disorders. In particular, T-cells are thought to be the cells that start and perpetuate autoimmune diseases. Autoimmune diseases are a group of serious, chronic illnesses that afflict millions of people in the United States alone. Autoimmune diseases are characterized by reactivity of the immune system to endogenous (self) antigens. These immune responses to self antigens are maintained by the persistent or recurrent activation of self-reactive T-cells and, directly or indirectly, the self-reactive T-cells are responsible for the characteristic tissue injury and destruction seen in autoimmune diseases. Although many treatments for autoimmune diseases and other T-cell mediated diseases have been proposed, there is still a need for additional treatments.

While the overall immune system provides the organism protection from physical injury and infectious agents, lack of control of the system can result in damage to the organisms own tissue. For example, following physical damage to the organism, the non-specific nature of the innate immune response often results in damage to normal health tissue. Similarly, over or under-active T-cell responses can result in auto immune diseases such as arthritis, bursitis, allergies, asthma, sepsis, shock and the like. Thus, tight control of immune response initiation and inhibition are critical to maintain health and numerous compounds have been developed to establish and maintain such control (e.g., cyclooxygenase inhibitors such as aspirin, ibuprofen, etc.), Diketopiperazines have been reported to exhibit a variety of biological activities. See, e.g., U.S. Pat. No. 4,289,759 (immunoregulatory agents), U.S. Pat. No. 4,331,595 (immunoregulatory agents), U.S. Pat. No. 4,940,709 (PAF antagonists), U.S. Pat. No. 5,700,804 (inhibitors of plasminogen activator inhibitor), U.S. Pat. No. 5,750,530 (inhibitors of plasminogen activator inhibitor), U.S. Pat. No. 5,990,112 (inhibitors of metalloproteases), PCT applications WO 97/36888 (inhibitors of farnesyl-protein transferase) and WO 99/40931 (treatment of central nervous system injury), EP application 43219 (immunoregulatory agents), Japanese application 63 290868 (PAF antagonists), Japanese application 31 76478 (immunosuppressive agents), Shimazaki et al., Chem. Pharm. Bull., 35(8), 3527-3530 (1987) (PAF antagonists), Shimazaki et al., J. Med. Chem., 30, 1709-1711 (1987) (PAF antagonists), Shimazaki et al., Lipids, 26(12), 1175-1178 (1991) (PAF antagonists), Yoshida et al., Prog. Biochem. Pharmacol., 22, 68-80 (1988) (PAF antagonists), Alvarez et al., J. Antibiotics, 47(11), 1195-1201 (1994) (inhibitors of calpain), the complete disclosures of which are incorporated herein by reference.

Many diketopiperazines are known. For example, the diketopiperazine composed of aspartic acid and alanine (3-methyl-2,5-diketopiperazine-6-acetic acid; DA-DKP) is known. It has been reported to be formed as a result of the degradation of human albumin stored above 30° C. Chan et al., Eur. J. Biochem., 227, 524-528 (1995). Moreover, the use of such diketopiperazines for treating diseases by manipulation of various aspects of the immune system is also known. However, there is still a need for improved methods for regulating the immune system and treating diseases. The present invention provides such methods.

SUMMARY OF THE INVENTION

One embodiment of the invention relates to a method of inhibiting inflammation by administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about 6 hours after administration of the pharmaceutical composition.

Another embodiment of the invention relates to a method of treating a T-cell mediated disease by administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about 6 hours after administration of the pharmaceutical composition.

In one aspect, the T-cell mediated disease is graft rejection, graft versus host disease, an unwanted delayed-type hypersensitivity reaction, a T-cell mediated pulmonary disease, an autoimmune disease or an inflammatory disease.

In another aspect, the T-cell-mediated disease is selected form the group consisting of multiple sclerosis, neuritis, polymyositis, psoriasis, vitiligo, Sjogren's syndrome, rheumatoid arthritis, Type 1 diabetes, autoimmune pancreatitis, inflammatory bowel diseases, Crohn's disease, ulcerative colitis, celiac disease, glomerulonephritis, scleroderma, sarcoidosis, autoimmune thyroid diseases, Hashimoto's thyroiditis, Graves disease, myasthenia gravis, Addison's disease, autoimmune uveoretinitis, pemphigus vulgaris, primary biliary cirrhosis, pernicious anemia and systemic lupus erythematosus.

In yet another aspect, the T-cell-mediated disease is pulmonary fibrosis or idiopathic pulmonary fibrosis.

In still another aspect, the T-cell-mediated disease is an inflammatory disease.

Yet another embodiment of the invention relates to a method of treating a joint disease or condition by administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about 6 hours after administration of the pharmaceutical composition.

In one aspect, the joint disease or condition is a degenerative joint disease.

Another embodiment of the invention relates to a method of reducing the level of interleukin-8 (IL-8) in an individual by administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about 6 hours after administration of the pharmaceutical composition.

In any of the embodiments of the invention described above or elsewhere herein, in one aspect, the LMWF of HSA contains components having a molecular weight less than 5000.

In any of the embodiments of the invention described above or elsewhere herein, in one aspect, the LMWF of HSA contains components having a molecular weight less than 3000.

In any of the embodiments of the invention described above or elsewhere herein, in one aspect, the LMWF of HSA comprises DA-DKP.

In any of the embodiments of the invention described above or elsewhere herein, in one aspect, the LMWF of HSA comprises one or more compounds selected from the group consisting of N-acetyl tryptophan and caprylic acid.

In any of the embodiments of the invention described above or elsewhere herein, in one aspect, the individual receiving the pharmaceutical composition is not administered a COX-2 antagonist within a time period selected from the group consisting of at least about one hour, at least about 12 hours, at least about one day, at least about two days, at least about three days, at least about four days, at least about five days, at least about six days, at least about seven days, at least about eight days or at least about nine days and 10 days, prior to administration of the pharmaceutical composition.

In any of the embodiments of the invention described above or elsewhere herein, in one aspect, the individual receiving the pharmaceutical composition is not administered a COX-2 antagonist during the period of time in which at least one active ingredient in the pharmaceutical composition exerts its effect. In one aspect, the composition that reduces COX-2 activity comprises a chemical selected from the group consisting of acetylsalicylic acid (aspirin), 2-(4-isobutylphenyl)propanoic acid (ibuprofen), N-(4-hydroxyphenyl)ethanamide (paracetamol), (S)-6-methoxy-α-methyl-2-naphthaleneacetic acid (naproxen), 2-[(2,6-dichlorophenyl)amino] benzeneacetic acid (diclofenac), 4-[5-(4-methylphenyl)-3-(trifluoromethyl)-1H-pyrazol-1-yl] benzenesulfonamide (celecoxib), 4-[4-(methyl sulfonyl) phenyl]-3-phenyl-2(5H)-furanone (rofecoxib), and 4-(5-Methyl-3-phenylisoxazol-4-yl)benzolsulfonamid (valdecoxib).

In any of the embodiments of the invention described above or elsewhere herein, in one aspect, the individual receiving the pharmaceutical composition is not administered a COX-2 antagonist within a time period selected from the group consisting of at least 6 hours, at least 12 hours, at least about 24 hours, at least about two days, at least about three days, at least about four days, at least about five days, at least about six days, at last about one week, at least about two weeks, at least about three weeks, at least about one month, at least about two months, at least about three months, at least about four months at least about five months or at least about six months after administration of a pharmaceutical composition of the invention.

DETAILED DESCRIPTION OF THE INVENTION

Figure 1A:
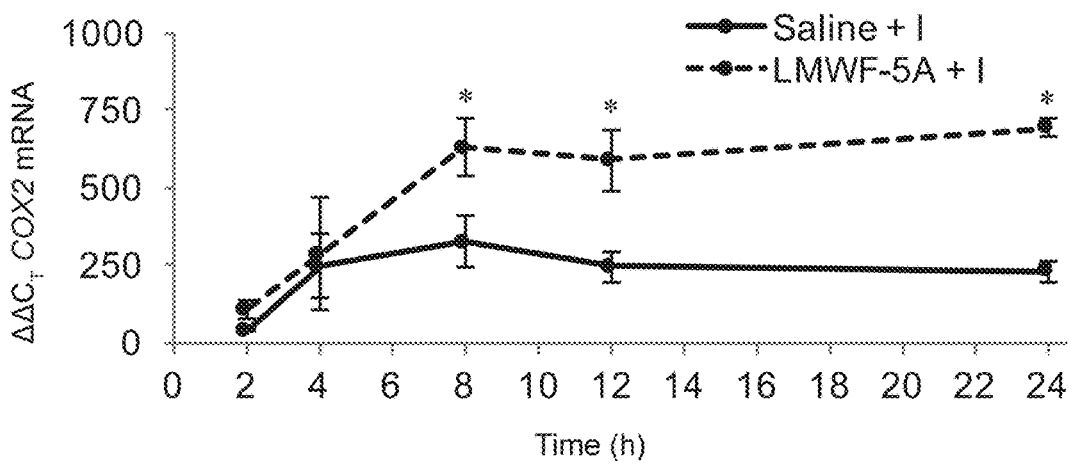
FIGS. 1A-1C show that the LMWF of HSA wherein at least one component comprises DA-DKP (also referred to herein as "LMWF-5A") increases COX2 mRNA in OA synoviocytes (primary synoviocytes isolated from the knee synovial membrane of patients with osteoarthritis (OA)) over a 24 h time course. OA synoviocytes were cultured in the presence of LMWF-5A or saline with 10 ng/mL IL-1β (FIG. 1A), LMWF-5A or saline with 10 ng/mL TNFα (FIG. 1B), or LMWF-5A or saline alone (FIG. 1C) for up to 24 h. Total RNA was harvested 2, 4, 8, 12, and 24 hours post-treatment, and qPCR was performed to quantify the total COX2 mRNA and 18S rRNA expression. Using the $\Delta\Delta C_T$ method, relative fold changes were quantified and normalized to untreated OA synoviocytes. The normalized fold-change (mean±SEM) is shown. * indicates significantly increased COX2 mRNA when compared to the saline control at that time point ($p<0.05$; n=4).
Figure 1B:
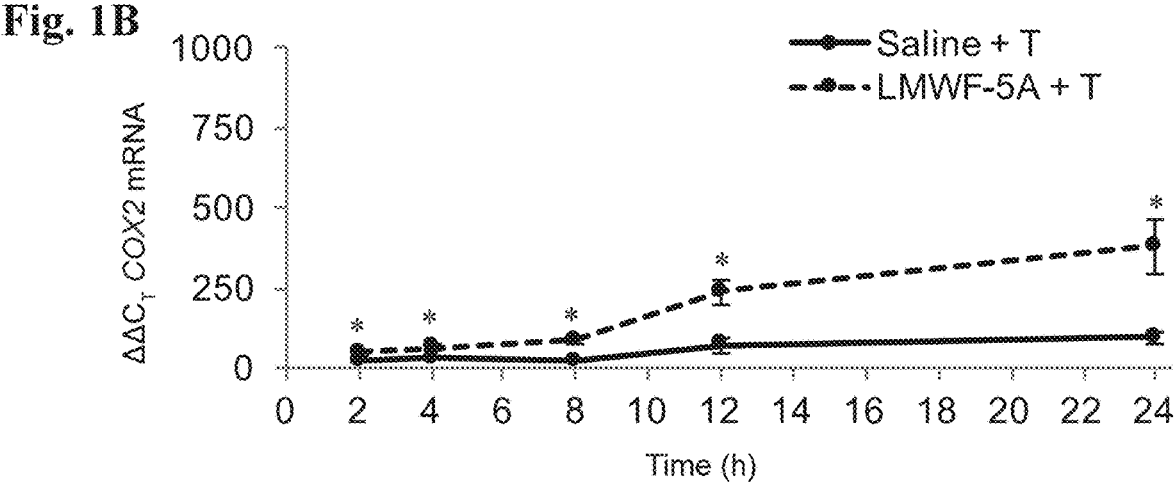

The present invention provides a method of modulating various aspects of the immune system. In particular, the present invention teaches the use of a low molecular weight fraction of a solution of human serum albumin, which includes aspartic acid-alanine-diketopiperazine (DKP) to modulate various aspects of the immune system such as, for example, T-cells and various cytokines. Because the composition disclosed herein is capable of modulating aspects of the immune system, it can therefore be used to treat various diseases and conditions. aspartic acid-alanine-diketopiperazine has Formula (I):

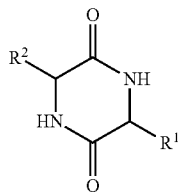

wherein:

$R^1$ and $R^2$ are different and each is the side chain of an amino acid selected from the group consisting of alanine and aspartic acid; or a physiologically-acceptable salt thereof. This diketopiperazine is referred to as DA-DKP (also referred to as aspartic acid-alanine-DKP or Asp-Ala-DKP or 3-methyl-2,5-diketopiperazine-6-acetic acid).

The present inventors have discovered that a low molecular weight fraction ("LMWF") of human serum albumin (HSA) functions by increasing levels of cyclooxygenase-2 (COX-2).

The term "LMWF" refers to a low molecular weight fraction of HSA that is a composition prepared by separation of high molecular weight components from human serum albumin (HSA). For example, LMWF can be prepared by filtration of a commercially available HSA solution wherein molecular weight components of more than 3 kilo daltons (kDa), 5 kDa, 10 kDa, 20 kDa, 30 kDa, 40 kDa, 50 kDa, are separated from the HSA solution. Alternatively, the term LMWF can refer to a composition prepared by separation of the high molecular weight components by other techniques, including but not limited to ultrafiltration, column chromatography including size exclusion chromatography, affinity chromatography, anion exchange, cation exchange, sucrose gradient centrifugation, salt precipitation, or sonication. LMWF also refers to a composition that includes components of HSA having a molecular weight less than 50,000 daltons (Da) (or 50 kDa), 40 kDa, 30 kDa, 20 kDa, 10 kDa, 5000 Da, 4000 Da, or 3000 Da (corresponding to 50,000 g/mol, 40,000 g/ml, 30,000 g/mol, 20,00 g/mol, 10,000 g/mol, 5,000 g/mol, 4,000 g/mol or 3,000 g/mol respectively).

At least one of the components in LMWF is DA-DKP.

In embodiments of the invention, individuals being treated with LMWF as disclosed herein do not receive any COX-2 antagonists prior or subsequently to administration of LMWF in a manner that a COX-2 antagonist does not interfere with the mechanism of action of LMWF which as has now been recognized by the inventor includes increasing levels of COX-2. Thus, a method of the present invention can generally be practiced by administering to an individual a composition comprising LMWF, wherein at the time of administration the individual's immune system is not being significantly affected by a COX-2 antagonist. That is, in the time period prior and/or subsequent to administration of the LMWF of HSA (e.g., 30 minutes, one hour, six hours, 12 hours, 24 hours, one day, one week, etc.) the individual being treated has not been administered, or has not self-administered, a compound that reduces or inhibits COX-2 activity.

DA-DKP is known to occur in solutions of human serum albumin and therefore, in LMWF of the present invention will occur because DA-DKP is a low molecular weight molecule. In certain embodiments, DA-DKP will be present in LMWF in concentrations ranging from about 0 μM DA-DKP to about 200 μM DA-DKP. In still other embodiments the DA-DKP will be present in LMWF in concentrations ranging from about 50 μM DA-DKP to about 100 μM DA-DKP. In addition, concentrations of DA-DKP in LMWF can be modified by addition of DA-DKP. For example, DA-DKP concentrations can be increased by methods described in U.S. Patent Publication No. 2015/0366932. Alternatively, DA-DKP can be made synthetically. Methods of preparing diketopiperazines, such as DA-DKP are known in the art, and such methods can be used to synthesize DA-DKP. See, e.g., See, e.g., U.S. Pat. Nos. 4,694,081, 5,817,751, 5,990,112, 5,932,579, U.S. Patent Publication No.2004/0024180, PCT Publication Nos. WO 96/00391 and WO 97/48645, and Smith et al., *Bioorg. Med. Chem. Letters*, 8, 2369-2374 (1998), the complete disclosures of which are incorporated herein by reference. In addition, DA-DKP can be synthesized by methods described in U.S. Patent Publication No. 2015/0366932.

In addition, the LMWF compositions of the present invention wherein at least one of the components of the LMWF comprises DA-DKP, will further comprise additional compounds. Examples of such compounds include, but are not limited to, N-acetyl tryptophan (NAT), caprylic acid, caprylate, or combinations thereof. The concentration of any one of N-acetyl tryptophan (NAT), caprylic acid, caprylate, or combinations thereof in the product can be in the range of about 4 mM to about 20 mM. The concentration of these components will be in the range of amounts that are found in commercial solutions of human serum albumin.

One embodiment of the present invention is a method of inhibiting inflammation, the method comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about 6 hours after administration of the pharmaceutical composition.

Another embodiment of the present invention is a method of treating a T-cell mediated disease, comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about 6 hours after administration of the pharmaceutical composition.

Another embodiment of the present invention is a method of preventing a T-cell mediated disease, comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about 6 hours after administration of the pharmaceutical composition.

As used herein, to treat means to reduce (wholly or partially) the symptoms, duration or severity of a disease, including curing the disease. In addition, the terms administering, administered, administer, and the like, are meant to encompass administration of a compound to an individual through self-administration or by another individual by any suitable method. For example, the term refers to contact of a compound with the individual being treated by, for example, methods such as oral ingestion, injection, infusion, application of a topical paste, nasally, rectally, vaginally, parenterally (e.g., intra-articular, intravenously, intraspinally, intraperitoneally, subcutaneously, or intramuscularly), intracisternally, transdermally, intracranially, intracerebrally, and topically (including buccally and sublingually). The composition of the present invention comprising a LMWF of HSA may be administered to an individual by any suitable route of administration, including locally, parenterally (e.g., injection, intra-articular injection, intravenously, intraspinally, intraperitoneally, subcutaneously, or intramuscularly), transdermally, and topically.

According to the present invention, T-cell mediated diseases are those resulting from an increase or decrease in the level of T-cells and/or T-cell activity. Examples of T-cell mediated diseases include, but are not limited to, graft rejection, graft versus host disease, unwanted delayed-type hypersensitivity reactions (such as delayed-type allergic reactions), T-cell mediated pulmonary diseases, and autoimmune diseases. T-cell mediated pulmonary diseases include sarcoidosis, hypersensitivity pneumonitis, acute interstitial pneumonitis, alveolitis, pulmonary fibrosis, idiopathic pulmonary fibrosis and other diseases characterized by inflammatory lung damage. Autoimmune diseases include multiple sclerosis, neuritis, polymyositis, psoriasis, vitiligo, Sjogren's syndrome, rheumatoid arthritis, Type 1 diabetes, autoimmune pancreatitis, inflammatory bowel diseases (e.g., Crohn's disease and ulcerative colitis), celiac disease, glomerulonephritis, scleroderma, sarcoidosis, autoimmune thyroid diseases (e.g., Hashimoto's thyroiditis and Graves disease), myasthenia gravis, Addison's disease, autoimmune uveoretinitis, pemphigus vulgaris, primary biliary cirrhosis, pernicious anemia, and systemic lupus erythematosis.

Pharmaceutical compositions useful for practicing the present invention can be administered in any form and by any method. Examples of useful routes of administration include, but are not limited to, orally, nasally, rectally, vaginally, parenterally (e.g., intravenously, intraspinally, intraperitoneally, subcutaneously, or intramuscularly), intracisternally, transdermally, intracranially, intracerebrally, and topically (including buccally and sublingually). Preferred routes of administration are orally and intravenously. Examples of useful forms of pharmaceutical compositions and routes of administration are described in detail in U.S. Pat. Nos. 8,183,209 and 8,980,834, the entirety of which are incorporated herein by reference.

In certain embodiments, the individual being treated is a mammal, such as a rabbit, goat, dog, cat, horse or human. In one embodiment, the individual is a human.

As has been described, for example in U.S. Pat. No. 8,183,209, diketopiperazines for use in the present invention can be prepared by heating solutions of albumin. The solution can be a concentrated solution (e.g., about 100-500 mM) to achieve protonation of the N-terminal and/or C-terminal amino acid. The solution is heated at, for example, 60° C. for from about 2 hours to several days, preferably about 4 days, to cause formation of the diketopiperazine. Thus, in one embodiment, prior to passing the albumin solution over the filtration device, the albumin solution is heated under conditions effective to cause formation of diketopiperazines. In one embodiment, the albumin solution is heated to at least 60° C.

The diseases and conditions disclosed herein, are treated by administering to individual in need thereof an effective amount of a pharmaceutical composition comprising a low molecular weight fraction (LMWF) of human serum albumin (HSA). In addition, the individual is not administered a cyclooxygenase-2 (COX-2) antagonist during the time of administration of the LMWF, such as within the period of time ranging from about one hour before to about 6 hours after administration of the pharmaceutical composition.

As previously discussed, pharmaceutical compositions of the invention can comprise additional compounds. In one embodiment, the pharmaceutical composition comprises N-acetyl tryptophan (NAT). In one embodiment, the pharmaceutical composition comprises caprylic acid and/or caprylate. In one embodiment, the pharmaceutical composition comprises at least one compound selected from the group consisting of NAT, caprylic acid, caprylate and mixture thereof.

Because the biological activity of the LMWF of HSA wherein at least one of the components is DA-DKP, is due, at least in part, to an increase in COX-2 activity, the individual to which the pharmaceutical composition is being administered should not have been administered, or should not have self-administered, a compound that reduces COX-2 activity prior or subsequent to administration of the pharmaceutical composition in a manner that substantially affects the biological activity of the LMWF. As used herein, a compound that reduces COX-2 activity is one that causes a reduction in the level of COX-2 enzymatic activity of at least about 10%, at last about 15%, at least about 20%, at least about 25%, at least about 30%, at least about 35%, at least about 40%, at least about 50%, at least about 60%, at least about 70%, at least about 80%, at last about 90%, at least about 95% or about 100% compared to the level of COX-2 enzymatic activity observed from a COX-2 enzyme not exposed to the LMWF. According to the present invention, a compound that reduces COX-2 activity can be referred to as a COX-2 antagonist and include known COX-2 inhibitors. COX-2 antagonists are known in the art, examples of which include, but are not limited to, acetylsalicylic acid (aspirin), 2-(4-isobutylphenyl)propanoic acid (ibuprofen), N-(4-hydroxyphenyl)ethanamide (paracetamol), (S)-6-methoxy-α-methyl-2-naphthaleneacetic acid (naproxen), 2-[(2,6-dichlorophenyl)amino] benzeneacetic acid (diclofenac), 4-[5-(4-methylphenyl)-3-(trifluoromethyl)-1H-pyrazol-1-yl] benzenesulfonamide (celecoxib), 4-[4-(methylsulfonyl)phenyl]-3-phenyl-2(5H)-furanone (rofecoxib), and 4-(5-Methyl-3-phenylisoxazol-4-yl)benzolsulfonamid (valdecoxib).

It is appreciated by those skilled in the art that COX-2 antagonist may be cleared from an individual's body at different rates. Such rates depend on the half-life, the time to steady state, the method of clearance, the species of the individual, and the like. For example, while naproxen can usually be cleared from the body in 4-5 days, complete clearance of aspirin can take 5 days. Of course, the time needed to eliminate a COX-2 antagonist to an insignificant level (i.e., the level at which no appreciable effect of the COX-2 antagonist on treatment with a pharmaceutical composition of the invention is observed) is affected by the size of the dose as well as whether one or multiple doses of the COX-2 antagonist were taken. In preferred embodiments, the time between when the final administration of a COX-2 antagonist (i.e., the last time a COX-2 antagonist was taken or administered) and the time of administration of a pharmaceutical composition of the invention is determined based on the pharmacokinetics of the particular COX-2 antagonist.

In one embodiment, the time period between final administration of a COX-2 antagonist and administration of a pharmaceutical composition of the invention is at least equal to the total clearance time (i.e., the time needed to reduce the level of the COX-2 antagonist in the individual being treated to an insignificant level) of the COX-2 antagonist. In one embodiment, the time period between final administration of a COX-2 antagonist and administration of a pharmaceutical composition of the invention is greater than the total clearance time of the COX-2 antagonist. In one embodiment, the time period between final administration of a COX-2 antagonist and administration of a pharmaceutical composition of the invention is at least 70%, at least 80%, at least 90%, or at least 95% of the total clearance time of the COX-2 antagonist.

In one embodiment, the individual receiving the pharmaceutical composition is not administered a COX-2 antagonist within a time period selected from the group consisting of at least about 15 minutes, at least about 30 minutes, at least about one hour, at least about two hours, at least about three hours, at least about four hours, at least about five hours, at least about six hours, at least about seven hours, at least about eight hours, at least about nine hours, at least about ten hours, at least about eleven hours, at least about twelve hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about one day or 24 hours, at least about two days, at least about three days, at least about four days, at least about five days, at least about six days, at least about seven days, at least about eight days or at least about nine days and 10 days, prior to (or before) administration of the pharmaceutical composition. As used herein, the word about, with particular reference to time values, refers to a variation of 10%. According to the present disclosure, time periods for exclusion of administration of a COX-2 antagonist prior to treatment with a pharmaceutical composition of the invention can be defined in ranges using any of the times disclosed herein. For example, in one embodiment, the individual receiving the pharmaceutical composition has not been administered, or self-administered, a COX-2 antagonist in time period ranging from at least about 15 minutes to 10 days prior to administration of the pharmaceutical composition. In various embodiments of the invention, the individual receiving the pharmaceutical composition has not been administered, or self-administered, a COX-2 antagonist in time period ranging from at least about 15 minutes to at least about one day, at least about two days, at least about three days, at least about four days, at least about five days, at least about six days, at least about seven days, at least about eight days or at least about nine days prior to (or before) administration of the pharmaceutical composition. In still other embodiments of the invention, the individual receiving the pharmaceutical composition has not been administered, or self-administered, a COX-2 antagonist in time period ranging from at least about 30 minutes to at least about one day, at least about two days, at least about three days, at least about four days, at least about five days, at least about six days, at least about seven days, at least about eight days or at least about nine days prior to (or before) administration of the pharmaceutical composition. Examples of further ranges include, but are not limited to at least about 15 minutes to at least about 24 hours, 15 minutes to at least about two days, 15 minutes to at least about three days, 15 minutes to at least about four days, 15 minutes to at least about five days, 15 minutes to at least about six days, 15 minutes to at least about seven days, at least about 30 minutes, to at least about 4-5 days, at least about one hours to at least about 4-6 days, at least about 2-4 hours to about 4-6 days. The ranges disclosed herein are only meant as illustrative examples and are not meant to limit the invention to the specific ranges disclosed herein.

In addition to excluding administration of a COX-2 antagonist within a range of time prior to administration of a pharmaceutical composition of the invention, those skilled in the art will understand that because the pharmaceutical composition of the invention has a range of time during which it is active, COX-2 antagonists should not be administered in a time period following (or after) administration of a pharmaceutical composition of the invention. Generally, this time period is the time period during which the active ingredient(s) of the pharmaceutical composition exert its/their effect. As used herein, an active ingredient is any ingredient present in the pharmaceutical composition that contributes to any of the biological effects disclosed herein (e.g., inhibiting T-cell activation, inhibiting inflammation, inhibiting PAF aggregation, etc.) For example, this time period can be the clearance time of the active ingredient(s) in the pharmaceutical composition. In one embodiment, the individual is not administered a COX-2 antagonist for at least about 2 hours, at least about 4 hours, at least about 6 hours, at least about 8 hours, at least about 10 hours, at least 12 hours, at least about 24 hours, at least about two days, at least about three days, at least about four days, at least about five days, at least about six days, at last about one week, at least about two weeks, at least about three weeks, at least about one month, at least about two months, at least about three months, at least about four months at least about five months or at least about six months after (or following) administration of a pharmaceutical composition of the invention. As noted above, time periods can also be stated in ranges comprising any of the times disclosed herein. For example, a time period during which an individual being treated can be excluded from administration of a COX-2 antagonist can include a period of time from 10 days prior to administration of a pharmaceutical composition of the invention to six months after administration of a pharmaceutical composition of the invention. In one embodiment, the individual being treated is not administered a COX2 antagonist during a time period ranging from 10 days prior to administration of a pharmaceutical composition of the invention to six months after administration of a pharmaceutical composition of the invention. Further examples of useful time periods include, but are not limited to a time period ranging from 10 days prior to administration of a pharmaceutical composition of the invention to six months after administration of a pharmaceutical composition of the invention; a time period ranging from 10 days prior to administration of a pharmaceutical composition of the invention to one week after administration of a pharmaceutical composition of the invention; a time period ranging from 10 days prior to administration of a pharmaceutical composition of the invention to two weeks after administration of a pharmaceutical composition of the invention; a time period ranging from 10 days prior to administration of a pharmaceutical composition of the invention to three weeks after administration of a pharmaceutical composition of the invention; a time period ranging from 10 days prior to administration of a pharmaceutical composition of the invention to four weeks after administration of a pharmaceutical composition of the invention; a time period ranging from 10 days prior to administration of a pharmaceutical composition of the invention to two months after administration of a pharmaceutical composition of the invention; a time period ranging from seven days prior to administration of a pharmaceutical composition of the invention to one week after administration of a pharmaceutical composition of the invention; a time period ranging from seven days prior to administration of a pharmaceutical composition of the invention to two weeks after administration of a pharmaceutical composition of the invention; a time period ranging from seven days prior to administration of a pharmaceutical composition of the invention to three weeks after administration of a pharmaceutical composition of the invention; a time period ranging from seven days prior to administration of a pharmaceutical composition of the invention to one month after administration of a pharmaceutical composition of the invention. Such time ranges are meant as illustrative examples only and are not meant to limit the invention as other time ranges can be used based on the times disclosed herein.

The LMWF of HSA disclosed herein is effective in treating T-cell mediated diseases because it inhibits, among other things, the activation of T-cells. "Inhibit" is used herein to mean to reduce (wholly or partially). Thus, one embodiment of the present invention is a method of inhibiting T-cell activation in an individual, comprising administering to an individual an effective amount of a pharmaceutical composition comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about six hours after administration of the pharmaceutical composition. In one aspect, the LMWF of HSA contains components having a molecular weight of less than 5000. In another aspect, the LMWF of HSA contains components having a molecular weight of less than 3000. In a preferred aspect, at least one of the components in the LMWF comprises DA-DKP. In one embodiment, the individual receiving the pharmaceutical composition has not been administered a composition that reduces COX-2 activity in a time period selected from the group consisting of at least about one hour, at least about 12 hours, at least about one day, at least about two days, at least about three days, at least about four days, at least about five days, at least about six days, at least about seven days, at least about eight days or at least about nine days and 10 days, prior to administration of the pharmaceutical composition. In still another aspect, the pharmaceutical composition further comprises at least one compound selected from the group consisting of NAT, caprylic acid, caprylate and mixtures thereof.

Because inflammation is exacerbated by, or involves, activated T-cells, the LMWF of HSA of the invention can be used to treat inflammation and inflammatory diseases and/or to prevent inflammation and inflammatory diseases. Thus, one embodiment of the present invention is a method of reducing inflammation in an individual, comprising administering to the individual an effective amount of a pharmaceutical composition comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about six hours after administration of the pharmaceutical composition. In one aspect, the LMWF of HSA contains components having a molecular weight of less than 5000. In another aspect, the LMWF of HSA contains components having a molecular weight of less than 3000. In a preferred aspect, at least one of the components in the LMWF comprises DA-DKP. In one embodiment, the individual receiving the pharmaceutical composition has not been administered a composition that reduces COX-2 activity in a time period selected from the group consisting of at least about one hour, at least about 12 hours, at least about one day, at least about two days, at least about three days, at least about four days, at least about five days, at least about six days, at least about seven days, at least about eight days or at least about nine days and 10 days, prior to administration of the pharmaceutical composition. In still another aspect, the pharmaceutical composition further comprises at least one compound selected from the group consisting of NAT, caprylic acid, caprylate and mixtures thereof.

One embodiment of the present invention is a method of reducing the severity and/or symptoms of multiple sclerosis comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about six hours after administration of the pharmaceutical composition. In one aspect, the LMWF of HSA contains components having a molecular weight of less than 5000. In another aspect, the LMWF of HSA contains components having a molecular weight of less than 3000. In a preferred aspect, at least one of the components in the LMWF comprises DA-DKP. In one embodiment, the individual receiving the pharmaceutical composition has not been administered a composition that reduces COX-2 activity in a time period selected from the group consisting of at least about one hour, at least about 12 hours, at least about one day, at least about two days, at least about three days, at least about four days, at least about five days, at least about six days, at least about seven days, at least about eight days or at least about nine days and 10 days, prior to administration of the pharmaceutical composition. In still another aspect, the pharmaceutical composition further comprises at least one compound selected from the group consisting of NAT, caprylic acid, caprylate and mixtures thereof.

Diketopiperazines, such as DA-DKP, have also been shown to inhibit platelet activating factor. (see, for example, U.S. Pat. Nos. 6,555,543, 8,455,517, 8,440,696 and 8,841,307, the disclosures of which are incorporated herein by reference). Platelet activating factor (PAF; 1-O-alkyl-2-acetyl-sn-glycerol-3-phosphorylcholine) is a potent inflammatory phospholipid mediator with a wide variety of biological activities. It is generated and released by basophils, monocytes, macrophages, polymorphonuclear leukocytes, eosinophils, neutrophils, natural killer lymphocytes, platelets and endothelial cells, as well as by renal and cardiac tissues under appropriate immunological and non-immunological stimulation. PAF mediates biological responses by binding to specific PAF receptors found in a wide variety of cells and tissues.

PAF also appears to play a role in pathological immune and inflammatory responses. Many published studies have provided evidence for the involvement of PAF in diseases, including arthritis, acute inflammation, asthma, allergic reactions, cardiovascular diseases, neoplastic diseases, endotoxic shock, pain, psoriasis, ophthalmic inflammation, ischemia, gastrointestinal ulceration, myocardial infarction, inflammatory bowel diseases, and acute respiratory distress syndrome. (See, for example, PCT application WO 94/04537 and U.S. Pat. No. 6,555,543).

Accordingly, one embodiment of the present invention is a method of inhibiting PAF in an individual, comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about six hours after administration of the pharmaceutical composition. In one aspect, the LMWF of HSA contains components having a molecular weight of less than 5000. In another aspect, the LMWF of HSA contains components having a molecular weight of less than 3000. In a preferred aspect, at least one of the components in the LMWF comprises DA-DKP. In one embodiment, the individual receiving the pharmaceutical composition has not been administered a composition that reduces COX-2 activity in a time period selected from the group consisting of at least about one hour, at least about 12 hours, at least about one day, at least about two days, at least about three days, at least about four days, at least about five days, at least about six days, at least about seven days, at least about eight days or at least about nine days and 10 days, prior to administration of the pharmaceutical composition. In still another aspect, the pharmaceutical composition further comprises at least one compound selected from the group consisting of NAT, caprylic acid, caprylate and mixtures thereof.

PAF has been reported to play a role in a variety of disease and conditions. Examples of such diseases and conditions include acute respiratory distress syndrome, allergies, arthritis, asthma, autoimmune diseases, bronchitis, cardiovascular disease, Crohn's disease, cystic fibrosis, emphysema, gastrointestinal ulceration, inflammation, inflammatory bowel disease, ischemia, multiple organ dysfunction syndrome, myocardial infarction, neoplastic diseases, ophthalmic inflammation, pain, psoriasis, respiratory infections, sepsis, shock, and ulcerative colitis. Thus, one embodiment of the present invention is a method of treating a disease or condition mediated by PAF, the method, comprising administering to an individual in need of such treatment an effective amount of a pharmaceutical composition comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about six hours after administration of the pharmaceutical composition. In one aspect, the LMWF of HSA contains components having a molecular weight of less than 5000. In another aspect, the LMWF of HSA contains components having a molecular weight of less than 3000. In a preferred aspect, at least one of the components in the LMWF comprises DA-DKP. In one embodiment, the individual receiving the pharmaceutical composition has not been administered a composition that reduces COX-2 activity in a time period selected from the group consisting of at least about one hour, at least about 12 hours, at least about one day, at least about two days, at least about three days, at least about four days, at least about five days, at least about six days, at least about seven days, at least about eight days or at least about nine days and 10 days, prior to administration of the pharmaceutical composition. In still another aspect, the pharmaceutical composition further comprises at least one compound selected from the group consisting of NAT, caprylic acid, caprylate and mixtures thereof. In one embodiment, the diseases is selected from the group consisting of acute respiratory distress syndrome, allergies, arthritis, asthma, autoimmune diseases, bronchitis, cardiovascular disease, Crohn's disease, cystic fibrosis, emphysema, gastrointestinal ulceration, inflammation, inflammatory bowel disease, ischemia, multiple organ dysfunction syndrome, myocardial infarction, neoplastic diseases, ophthalmic inflammation, pain, psoriasis, respiratory infections, sepsis, shock, and ulcerative colitis.

PAF also mediates platelet aggregation. Thus, one embodiment of the present invention is a method of inhibiting platelet aggregation in an individual, the method, comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about six hours after administration of the pharmaceutical composition. In one aspect, the LMWF of HSA contains components having a molecular weight of less than 5000. In another aspect, the LMWF of HSA contains components having a molecular weight of less than 3000. In a preferred aspect, at least one of the components in the LMWF comprises DA-DKP. In one embodiment, the individual receiving the pharmaceutical composition has not been administered a composition that reduces COX-2 activity in a time period selected from the group consisting of at least about one hour, at least about 12 hours, at least about one day, at least about two days, at least about three days, at least about four days, at least about five days, at least about six days, at least about seven days, at least about eight days or at least about nine days and 10 days, prior to administration of the pharmaceutical composition. In still another aspect, the pharmaceutical composition further comprises at least one compound selected from the group consisting of NAT, caprylic acid, caprylate and mixtures thereof.

One embodiment of the present invention is a method of reducing the level of IL-8 in an individual, the method, comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about six hours after administration of the pharmaceutical composition. In one aspect, the LMWF of HSA contains components having a molecular weight of less than 5000. In another aspect, the LMWF of HSA contains components having a molecular weight of less than 3000. In a preferred aspect, at least one of the components in the LMWF comprises DA-DKP. In one embodiment, the individual receiving the pharmaceutical composition has not been administered a composition that reduces COX-2 activity in a time period selected from the group consisting of at least about one hour, at least about 12 hours, at least about one day, at least about two days, at least about three days, at least about four days, at least about five days, at least about six days, at least about seven days, at least about eight days or at least about nine days and 10 days, prior to administration of the pharmaceutical composition. In still another aspect, the pharmaceutical composition further comprises at least one compound selected from the group consisting of NAT, caprylic acid, caprylate and mixtures thereof.

One embodiment of the present invention is a method of altering the level of $PGE_2$, $PGI_1$, $PGF_{2\alpha}$, $PGD_2$, $15d\text{-}PGJ_2$, PPAR-$\gamma$, Ras, Erk, or a pathway affected thereby, in an individual, the method comprising administering to the individual an effective amount of a pharmaceutical composition comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about six hours after administration of the pharmaceutical composition. In one embodiment, the level of $PGE_2$, $PGI_1$, $PGF_{2\alpha}$, $PGD_2$, $15d\text{-}PGJ_2$, PPAR-$\gamma$, Ras or Erk, is increased. In one embodiment, the level of $PGE_2$, $PGI_1$, $PGF_{2\alpha}$, $PGD_2$, $15d\text{-}PGJ_2$, PPAR-$\gamma$, Ras or Erk, is decreased. In one aspect, the LMWF of HSA contains components having a molecular weight of less than 5000. In another aspect, the LMWF of HSA contains components having a molecular weight of less than 3000. In a preferred aspect, at least one of the components in the LMWF comprises DA-DKP. In one embodiment, the individual receiving the pharmaceutical composition has not been administered a composition that reduces COX-2 activity in a time period selected from the group consisting of at least about one hour, at least about 12 hours, at least about one day, at least about two days, at least about three days, at least about four days, at least about five days, at least about six days, at least about seven days, at least about eight days or at least about nine days and 10 days, prior to administration of the pharmaceutical composition. In still another aspect, the pharmaceutical composition further comprises at least one compound selected from the group consisting of NAT, caprylic acid, caprylate and mixtures thereof.

PAF has been reported to induce the production and secretion of interleukin 8 (IL-8). IL-8 is a pro-inflammatory cytokine which has been reported to play a role in the pathogenesis of a large number of diseases and conditions, including acute respiratory distress syndrome, allergies, arthritis, asthma, autoimmune diseases, bronchitis, cancer, Crohn's disease, cystic fibrosis, emphysema, endocarditis, gastritis, inflammatory bowel disease, ischemia reperfusion, multiple organ dysfunction syndrome, nephritis, pancreatitis, respiratory viral infections, sepsis, shock, ulcerative colitis, and other inflammatory disorders. One embodiment of the present invention is a method of treating an IL-8-mediated disease in an individual, the method, comprising administering to the individual an effective amount of a pharmaceutical composition comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about six hours after administration of the pharmaceutical composition. As used herein, an IL-8-mediated disease is one in which the signs and/or symptoms result, at least in part, from the action of IL-8. In one aspect, the LMWF of HSA contains components having a molecular weight of less than 5000. In another aspect, the LMWF of HSA contains components having a molecular weight of less than 3000. In a preferred aspect, at least one of the components in the LMWF comprises DA-DKP. In one embodiment, the individual receiving the pharmaceutical composition has not been administered a composition that reduces COX-2 activity in a time period selected from the group consisting of at least about one hour, at least about 12 hours, at least about one day, at least about two days, at least about three days, at least about four days, at least about five days, at least about six days, at least about seven days, at least about eight days or at least about nine days and 10 days, prior to administration of the pharmaceutical composition. In still another aspect, the pharmaceutical composition further comprises at least one compound selected from the group consisting of NAT, caprylic acid, caprylate and mixtures thereof.

Compositions of the invention can also be used to treat joint conditions. Examples of such treatment have been shown, for example, in U.S. Pat. No. 8,980,834, the entirety of which is incorporated herein by reference. Thus, one embodiment of the present invention is a method of treating a joint condition in an individual, the method comprising administering to the individual an effective amount of a pharmaceutical composition comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about six hours after administration of the pharmaceutical composition. In one aspect, the LMWF of HSA contains components having a molecular weight of less than 5000. In another aspect, the LMWF of HSA contains components having a molecular weight of less than 3000. In a preferred aspect, at least one of the components in the LMWF comprises DA-DKP. In one embodiment, the individual receiving the pharmaceutical composition has not been administered a composition that reduces COX-2 activity in a time period selected from the group consisting of at least about one hour, at least about 12 hours, at least about one day, at least about two days, at least about three days, at least about four days, at least about five days, at least about six days, at least about seven days, at least about eight days or at least about nine days and 10 days, prior to administration of the pharmaceutical composition. In still another aspect, the pharmaceutical composition further comprises at least one compound selected from the group consisting of NAT, caprylic acid, caprylate and mixtures thereof.

As used herein, a joint condition can include one or more of inflammation, T-cells, B-cells, cytokine production, edema, pyrexia, pain and the like. Examples of joint conditions treatable using compositions of the present invention include, but are not limited to, ankylosing spondylitis, Behcet's syndrome, arthritis, rheumatoid arthritis, osteoarthritis, psoriatic arthritis and swelling due to trauma (e.g., dislocation, fracture, etc.) Any joint can be treated using a composition of the invention. Examples include, but are not limited to, toe joints, knee joints, hip joints, spinal joints, finger joints, hand joints, wrist joints, elbow joints, shoulder joints and neck joints. Further, compositions of the invention can be administered using any route of administration resulting in delivery of the composition into the joint. For example, in one embodiment a composition of the invention is injected directly into the synovial cavity (intra-articular injection).

One specific example of a joint condition is degenerative joint disease. A degenerative joint disease is a gradual deterioration of the articular cartilage that covers joints. A degenerative joint disease is a noninfectious progressive disorder of the weightbearing joints. The normal articular joint cartilage is smooth, white, and translucent. It is composed of cartilage cells (chondrocytes) imbedded in a sponge-like matrix made of collagen, protein polysaccharides, and water. With early primary arthritis, the cartilage becomes yellow and opaque with localized areas of softening and roughening of the surfaces. As degeneration progresses, the soft areas become cracked and worn, exposing bone under the cartilage. The bone then begins to remodel and increase in density while any remaining cartilage begins to fray. Eventually, osteophytes (spurs of new bone) covered by cartilage form at the edge of the joint. As mechanical wear increases, the cartilage needs repairing. The cartilage cells are unable to produce enough of the sponge-like matrix and therefore the damaged cartilage cannot repair itself. The cartilage has no blood supply to enhance healing. The majority of degenerative joint disease is the result of mechanical instabilities or aging changes within the joint. This includes old age degenerative arthritis and, in younger individuals, may be the result of injuries, bruises, abnormal joint configuration (i.e. hip dysplasia), or mechanical wear from anterior cruciate ligament rupture, patellar luxation, or osteochondritis dissecans, for example. One embodiment of the present invention is a method of treating degenerative joint disease in an individual, the method comprising administering to the individual an effective amount of a pharmaceutical composition comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about six hours after administration of the pharmaceutical composition. In one aspect, the LMWF of HSA contains components having a molecular weight of less than 5000. In another aspect, the LMWF of HSA contains components having a molecular weight of less than 3000. In a preferred aspect, at least one of the components in the LMWF comprises DA-DKP. In one embodiment, the individual receiving the pharmaceutical composition has not been administered a composition that reduces COX-2 activity in a time period selected from the group consisting of at least about one hour, at least about 12 hours, at least about one day, at least about two days, at least about three days, at least about four days, at least about five days, at least about six days, at least about seven days, at least about eight days or at least about nine days and 10 days, prior to administration of the pharmaceutical composition. In still another aspect, the pharmaceutical composition further comprises at least one compound selected from the group consisting of NAT, caprylic acid, caprylate and mixtures thereof.

While surgery on joint a joint usually results in repair of an underlying problem, the physical trauma of the surgery itself usually causes swelling of the joint accompanied by an immune response. Pharmaceutical compositions can be used to treat joints following surgery. One embodiment of the present invention is a method of reducing a post-surgical immune response, post-surgical swelling and/or post-surgical pain in a joint, the method comprising administering to the individual an effective amount of a pharmaceutical composition comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about six hours after administration of the pharmaceutical composition. In one aspect, the LMWF of HSA contains components having a molecular weight of less than 5000. In another aspect, the LMWF of HSA contains components having a molecular weight of less than 3000. In one embodiment, the individual receiving the pharmaceutical composition has not been administered a composition that reduces COX-2 activity in a time period selected from the group consisting of at least about one hour, at least about 12 hours, at least about one day, at least about two days, at least about three days, at least about four days, at least about five days, at least about six days, at least about seven days, at least about eight days or at least about nine days and 10 days, prior to administration of the pharmaceutical composition. In still another aspect, the pharmaceutical composition further comprises at least one compound selected from the group consisting of NAT, caprylic acid, caprylate and mixtures thereof.

It should be understood that treatment of a joint for an immune response, swelling, etc., due to surgical trauma can be administered to the individual undergoing surgery before or immediately after surgery. Moreover, it should be understood that the pharmaceutical composition can be administered starting before surgery and continuing on a time course following surgery. In one embodiment, the pharmaceutical composition is administered prior to surgery. In one embodiment, the pharmaceutical composition is administered starting at about 3 days, about two days, about one day, about twelve hours, about six hours or about three hours prior to surgery. In one embodiment, the pharmaceutical composition is administered for at least about one day, for at least about two days, for at least three days about 3 days, for at least about four days, for at least about five days, for at least about six days, for at least about one week, for at least about two weeks, for at least about three weeks or for at least about four weeks following surgery.

Because the treatment of the present invention provides a long-lasting effect on the symptoms of degenerative joint disease, one aspect of the present invention is that a pharmaceutical composition of the invention can be administered to an individual at longer time intervals than would be expected for conventional therapies, wherein the individual has not been administered a compound that reduces COX-2 activity in the at least ten, the at least nine, the at least eight, the at least seven days, the at least six days, the at least five days, the at least four days, the at least three days, the at least two days, the at least 24 hours, the at least 12 hours, the at least six hours, the at least five hours, the at least four hours, the at least three hours, the at least two hours, the at least one hour, the at least 30 minutes, the at least 15 minutes and the at least ten minutes prior to administration of the pharmaceutical composition. In one embodiment, a pharmaceutical composition of the invention can be administered to an individual at longer time intervals than would be expected for conventional therapies, wherein the pharmaceutical composition further comprises at least one compound selected from the group consisting of NAT, caprylic acid, caprylate and mixtures thereof, and wherein the individual has not been administered a compound that reduces the activity of cyclooxygenase-2 (COX-2) in the at least 15 minutes prior to administration of the pharmaceutical composition. For example, the present composition can be administered no more frequently than once every six months once every five months, once every four months, once every three months, once every two months, once every month, once every four weeks, once every three weeks, once every two weeks or once every week.

It will be appreciated by those skilled in the art that because a pharmaceutical composition of the invention can be used in multiple treatments and for extended treatments of a disease or condition, in some embodiments the patient to which the pharmaceutical composition has been administered should not be administered a COX-2 antagonist for some period do time following administration of the pharmaceutical composition. The exact period of time will depend on the individual patent's ability to clear various compounds, including the compounds in a pharmaceutical composition of the invention e.g., LMWF of HSA, caprylate, N-acetyltryptophan). In one embodiment, a patient administered a pharmaceutical composition of the invention is not administered a COX-2 antagonist for at least one hour, at least two hours, at least three hours, at least four hours, at least five hours, at least six hours, at least 12 hours, at least one day, at least two days, at least three days, at least four days, at least five days, at least six days, at least one week, at least two weeks, at least three weeks or at least one month following administration of the pharmaceutical composition.

The composition of the present invention may be a pharmaceutical solution having a LMWF of HSA wherein at least one component of the LMWF comprises DA-DKP wherein the DA-DKP concentration range with a lower endpoint of about 10 µM, about 20 µM, about 30 µM, about 40 µM, about 50 µM, about 60 µM, about 70 µM, about 80 µM, about 90 µM, about 100 µM, about 110 µM, about 120 µM, about 130 µM, about 140 µM, about 150 µM, about 160 µM, about 170 µM, about 180 µM, about 190 µM, about 200 µM, about 210 µM, about 220 µM, about 230 µM, about 240 µM, about 240, about 250 µM, about 260 µM, about 270 µM, about 280 µM, about 290 µM, about 300 µM, about 310, about 320 µM, about 330 µM, about 340 µM, about 350 µM, about 360 µM, about 370 µM, about 380 µM, about 390 µM, or about 400 µM. The composition of the present invention may be a pharmaceutical solution having a DA-DKP concentration range with an upper endpoint of about 600 µM, about 580 µM, about 570 µM, about 560 µM, about 550 µM, about 540 µM, about 530 µM, about 520 µM, about 510 µM, about 500 µM, about 490 µM, about 480 µM, about 470 µM, about 460 µM, about 450 µM, about 440 µM, about 430 µM, about 420 µM, about 410 µM, about 400 µM, about 390 µM, about 380 µM, about 370 µM, about 360 µM, about 350, about 340 µM, about 330 µM, about 320 µM, about 310 µM, about 300 µM, about 290 µM, about 280 µM, about 270 µM, about 260 µM, about 250 µM, about 240 µM, about 230 µM, about 220 µM, about 210 µM, or about 200 µM.

An effective amount of the DA-DKP in the LMWF of HSA in the composition of the present invention for treating a degenerative joint disease or condition can be a range with a lower endpoint of about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, about 230 µg, about 240 µg, about 250 µg, about 260 µg, about 270 µg, about 280 µg, about 290 µg, about 300 µg, about 310 µg, about 320 µg, about 330 µg, about 340 µg, about 350 µg, about 360 µg, about 370 µg, about 380 µg, about 390 µg, about 400 µg, about 425 µg, about 450 µg, about 475 µg or about 500 µg. In addition, an effective amount of DA-DKP in the composition of the present invention for treating a degenerative joint disease or condition can be a range with upper endpoint of about 500 µg, about 490 µg, about 480 µg, about 470 µg, about 460 µg, about 450 µg, about 440 µg, about 430 µg, about 420 µg, about 410 µg, about 400 µg, about 390 µg, about 380 µg, about 370 µg, about 360 µg, about 350 µg, about 340 µg, about 330 µg, about 320 µg, about 310 µg, about 300 µg, about 290 µg, about 280 µg, about 270 µg, about 260 µg, about 250 µg, about 240 µg, about 230 µg, about 220 µg, about 210 µg, about 200 µg, about 190 µg, about 180 µg, about 170 µg, about 160 µg, about 150 µg, about 140 µg, about 130 µg, about 120 µg, about 110 µg, about 100 µg, about 90 µg, about 80 µg, about 70 µg, about 60 µg, about 50 µg, about 40 µg, about 30 µg, or about 20 µg.

Dosage forms for the topical or transdermal administration of compounds of the invention include powders, sprays, ointments, pastes, creams, lotions, gels, solutions, patches, and drops. The active ingredient may be mixed under sterile conditions with a pharmaceutically-acceptable carrier, and with any buffers, or propellants which may be required.

The ointments, pastes, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

While it is possible for a compound of the present invention to be administered alone, it is preferable to administer the compound as a pharmaceutical formulation (composition). The pharmaceutical compositions of the invention comprise a compound or compounds of the invention as an active ingredient in admixture with one or more pharmaceutically-acceptable carriers and, optionally, with one or more other compounds, drugs or other materials. Each carrier must be "acceptable" in the sense of being compatible with the other ingredients of the formulation and not injurious to the animal. Pharmaceutically-acceptable carriers are well known in the art. Regardless of the route of administration selected, the compounds of the present invention are formulated into pharmaceutically-acceptable dosage forms by conventional methods known to those of skill in the art. See, e.g., Remington's Pharmaceutical Sciences.

HSA has been used for fluid resuscitation and, more recently, for chronic liver and renal failure (Rozga J, et al. Human albumin: old, new, and emerging applications. *Ann Transplant* 2013, 18:205-217), and the fraction of 5% HSA under 5,000 Daltons, LMWF of HSA, has been shown to inhibit the release of inflammatory cytokines (Thomas G W, et al. Anti-Inflammatory Activity in the Low Molecular Weight Fraction of Commercial Human Serum Albumin (LMWF5A). *J Immunoassay Immunochem* 2016, 37(1):55-67; Bar-Or D, et al. Commercial human albumin preparations for clinical use are immunosuppressive in vitro. *Crit Care Med* 2006, 34(6):1707-1712). Clinical trials, in which the efficacy and safety of LMWF of HSA as a treatment for osteoarthritis of the knee were tested, have shown that injection of LMWF of HSA into the knee joint improves function and decreases pain in osteoarthritic knees, implicating an anti-inflammatory mode of action in vivo ((Rozga J, et al. Human albumin: old, new, and emerging applications. *Ann Transplant* 2013, 18:205-217). Other anti-inflammatory drugs, such as NSAIDs, have long been used to treat pain and swelling in osteoarthritis (Amoako A O, Pujalte G G: Osteoarthritis in young, active, and athletic individuals. *Clin Med Insights Arthritis Musculoskelet Disord* 2014, 7:27-32). Thus, the inventors concluded that LMWF of HSA may have a mechanism of action that is similar to that of NSAIDs, i.e., blocking the enzymatic function of COX2 and the subsequent downstream production of PGs (Botting R M: Vane's discovery of the mechanism of action of aspirin changed our understanding of its clinical pharmacology. *Pharmacol Rep* 2010, 62(3):518-525). As discussed in Example 1 below, the inventors have found that unexpectedly, LMWF of HSA super-induces COX2 when HSF-OAs are stimulated with either IL-1$\beta$ or TNF$\alpha$. They also observed a more pronounced response in IL-1$\beta$-stimulated, LMWF of HSA-treated HSF-OAs as compared to TNF$\alpha$-stimulated, LMWF of HSA-treated cells. Several cytokines and chemokines, including IL-1$\beta$ and TNF$\alpha$, have been implicated in the progression of OA; however, important differences exist between IL-1$\beta$ and TNF$\alpha$ with respect to OA. Increased IL-1$\beta$ levels are found in OA sera compared to normal sera (Sohn D H, et al: Plasma proteins present in osteoarthritic synovial fluid can stimulate cytokine production via Toll-like receptor 4. *Arthritis Res Ther* 2012, 14(1):R7), and synovial membrane and cartilage samples from patients with OA show higher levels of IL-1$\beta$-converting enzyme, which is required to process the precursor form of IL-1$\beta$ into mature cytokine (Saha N, et al. Interleukin-1beta-converting enzyme/caspase-1 in human osteoarthritic tissues: localization and role in the maturation of interleukin-1beta and interleukin-18. *Arthritis Rheum* 1999, 42(8): 1577-1587). In a mouse model of arthritis, IL-1 blockade prevents further disease progression, whereas inhibition of TNF$\alpha$ only decreases inflammation within the joint (Joosten L A, et al. IL-1 alpha beta blockade prevents cartilage and bone destruction in murine type II collagen-induced arthritis, whereas TNF-alpha blockade only ameliorates joint inflammation. *J Immunol* 1999, 163(9):5049-5055). TNF$\alpha$ is significantly increased in OA synovial fluid when compared to normal synovial fluid but is absent in OA sera (Sohn D H, et al: Plasma proteins present in osteoarthritic synovial fluid can stimulate cytokine production via Toll-like receptor 4. *Arthritis Res Ther* 2012, 14(1):R7). The inventors observed differences in the effects of IL-1$\beta$ versus TNF$\alpha$ stimulation in the presence of LMWF of HSA were pronounced with respect to COX2. Induction of COX2 in IL-1$\beta$-stimulated, LMWF of HSA-treated cells was much higher compared to TNF$\alpha$-stimulated, LMWF of HSA-treated cells; however, quantification of PGE2 release from IL-1$\beta$-stimulated cells in the presence of LMWF of HSA showed no significant difference. It was only under TNF$\alpha$-stimulated, LMWF of HSA-treated conditions that a significant increase in PGE2 was observed. It is important to note that the relative levels of PGE2 were 10-fold higher under IL-1$\beta$-stimulated conditions.

Considering that COX2 expression and PGE2 production are either the same or increased with LMWF-5A under pro-inflammatory cytokine conditions, one may expect that LMWF of HSA injection into the OA knee would elicit a localized inflammatory response. Eliciting an inflammatory response as a treatment has been coined as prolotherapy, which is characterized by redness, swelling, and pain following injections of prolotherapeutics, such as hypertonic dextrose and morrhuate sodium (Rabago D, Patterson J J: Prolotherapy: an effective adjunctive therapy for knee osteoarthritis. *J Am Osteopath Assoc* 2013, 113(2):122-123). The premise of prolotherapy is to elicit an inflammatory response that acts to trigger resolution and healing signaling cascades. Based on clinical trial data, LMWF of HSA does not cause a localized inflammatory response in vivo, as patients do not experience joint swelling but do experience rapid pain relief that persists 12 weeks post-injection (Bar-Or D, et al: A randomized clinical trial to evaluate two doses of an intra-articular injection of LMWF-5A in adults with pain due to osteoarthritis of the knee. *PLoS One* 2014, 9(2):e87910). Additional evidence that LMWF of HSA does not elicit an acute inflammatory response is that PBMCs stimulated with lipopolysaccharide release significantly less TNFα into the medium when co-treated with LMWF of HSA (Thomas G W, et al. Anti-Inflammatory Activity in the Low Molecular Weight Fraction of Commercial Human Serum Albumin (LMWF5A). *J Immunoassay Immunochem* 2016, 37(1):55-67), and treatment of HSF-OAs with LMWF of HSA and either IL-1β or TNFα does not increase IL-1β release into the media.

Because the inventors did not observe hallmarks of an acute inflammatory response either in vivo or in vitro, LMWF of HSA may circumvent this response and directly initiate healing and regeneration in the knee. Recent evidence has shown that inhibiting PGE2 degradation, thus increasing the tissue PGE2 concentration, potentiates multi-tissue regeneration and increases hematopoiesis and bone marrow stem cell fitness (Zhang Y, et al: TISSUE REGENERATION. Inhibition of the prostaglandin-degrading enzyme 15-PGDH potentiates tissue regeneration. *Science* 2015, 348(6240):aaa2340). Fibroblasts found in the synovial fluid are closely related to bone marrow stem cells (Jones E A, et al. Enumeration and phenotypic characterization of synovial fluid multipotential mesenchymal progenitor cells in inflammatory and degenerative arthritis. *Arthritis Rheum* 2004, 50(3):817-827) and may be a source of resident stem cells within the knee. Previously, the inventors have shown that LMWF of HSA drives chondrocyte condensation in human mesenchymal stem cells (hMSCs) (Bar-Or D, et al. Low Molecular Weight Fraction of Commercial Human Serum Albumin Induces Morphologic and Transcriptional Changes of Bone Marrow-Derived Mesenchymal Stem Cells. *Stem Cells Transl Med* 2015, 4(8):945-955), and inhibition of COX2 disrupts hMSC chondrogenesis (Pountos I, et al. NSAIDS inhibit in vitro MSC chondrogenesis but not osteogenesis: implications for mechanism of bone formation inhibition in man. *J Cell Mol Med* 2011, 15(3):525-534). Thus, injection of LMWF of HSA may influence multiple cell populations within the knee, synoviocytes, resident stem cells, and chondrocytes, to regenerate damaged cartilage through upregulation of COX2 and PGE2. Furthermore, we observed a significant increase in PGD2 release from LMWF of HSA-treated HSF-OAs under IL-1β and TNFα conditions. Increased PGD2 may trigger an anti-inflammatory/pro-resolution cascade, as it spontaneously undergoes non-enzymatic dehydration and is converted into 15-deoxy-$\Delta^{12,14}$-prostaglandin J2 (15d-PGJ2), a cyclopentenone PG that has been shown to be immunomodulatory and anti-inflammatory by its ability to inhibit NFκB signaling and cytokine release and to act as an agonist of PPARRγ (Buckley C D, et al. Proresolving lipid mediators and mechanisms in the resolution of acute inflammation. *Immunity* 2014, 40(3):315-327). The inventors attempted to measure 15d-PGJ2 using a commercially available competitive ELISA but found that LMWF of HSA interfered with quantification, resulting in artificially increased values. Nonetheless, the data presented herein clearly shows that LMWF of HSA significantly increases anti-inflammatory PGD2 release. Since increased release of PGs may be a key aspect of the therapeutic action of LMWF of HSA and because NSAIDs inhibit the production of all subclasses of PGs due to the inhibition of upstream COX2 enzymatic action, these results have influenced a current clinical trial evaluating LMWF of HSA, resulting in the exclusion of NSAID use by trial participants (NCT02556710).

The following experimental results are provided for purposes of illustration and are not intended to limit the scope of the invention.

EXAMPLES

Example 1

The ability to decrease inflammation and promote healing is important in the intervention and management of a variety of disease states, including osteoarthritis of the knee (OAK). Even though COX2 has an established pro-inflammatory role, evidence suggests it is also critical to the resolution that occurs after the initial activation phase of the immune response. In this example, the effects of the LMWF of HSA wherein at least one of the components of the LMWF comprises DA-DKP, an agent that has proven to decrease pain and improve function in OAK patients after intra-articular injection, was studied on the expression of COX2 and its downstream products, prostaglandins (PGs).

In the inflammatory environment of OAK, LMWF of HSA (LMWF-5A) treated synoviocytes increase their expression of COX2 and the downstream prostaglandins PGE2 and PGD2. Importantly, no inflammatory responses have been observed in either OAK patients or cell culture upon intra-articular injection or treatment with LMWF-5A. LMWF-5A is believed to increase COX2 and downstream PGE2 release from synoviocytes into the synovial fluid, inducing regeneration of cartilage, as they have been implicated in promoting chondrogenesis and tissue regeneration. Furthermore, the inventors have previously shown that LMWF-5A increases chondrocyte condensation in stem cells. Additionally, increased PGD2 release from synoviocytes observed upon LMWF-5A treatment may trigger resolution of inflammation and healing via NFκB inhibition and PPARγ activation.

Fibroblast-like synoviocytes from the synovial membrane of OAK patients were treated with LMWF of HSA or saline as a control with or without the addition of cytokine (interleukin-1β [IL-1β] or tumor necrosis factor α [TNFα]) to elicit an inflammatory response. Cells were harvested for RNA and protein at 2, 4, 8, 12, and 24 h, and media was collected at 24 h for analysis of secreted products. COX2 mRNA expression was determined by qPCR, and COX2 protein expression was determined by western blot analysis. Levels of prostaglandin E2 (PGE2) and prostaglandin D2 (PGD2) in the media were quantified by competitive ELISA. In the presence of cytokine, LMWF of HSA increased the expression of both COX2 mRNA and protein, and this increase was significant compared to that observed with cytokine alone. Downstream of COX2, the levels of PGE2 were increased only in TNFα-stimulated cells; however, in both IL-1β- and TNFα-stimulated cells, LMWF of HSA increased the release of the anti-inflammatory PGD2. Thus, the LMWF of HSA appears to trigger increased anti-inflammatory PG signaling, and this may be a primary component of its therapeutic mode of action in the treatment of OAK.

Methods for Example 1:

The LMWF of HSA was produced at Ampio Pharmaceuticals (Englewood, Colo.) as previously described by Bar-Or (Bar-Or, D. et al: A randomized clinical trial to evaluate two doses of an intra-articular injection of LMWF-5A in adults with pain due to osteoarthritis of the knee. *PLoS One* 2014, 9(2):e87910). Briefly, 5% HSA (Octapharma, Hoboken, N.J.) was subjected to tangential flow filtration through a PVDF membrane with a 5 kDa molecular weight cutoff. The <5 kDa fraction was aseptically filled into glass vials, sealed, and stored in the dark at room temperature.

Cell Culture

Human synovial fibroblasts from patients with osteoarthritis (HSF-OA; Asterand, Detroit, Mich.) were maintained in Dulbecco's Modified Eagle Medium/Nutrient Mixture F-12 (DMEM/F12; ThermoFisher Scientific, Waltham, Mass.) containing 20% fetal bovine serum (FBS). Before plating for experiments, the cells were fed every two to three days with media containing 10% FBS for two media changes.

For the time course of COX2 mRNA and protein expression, HSF-OAs ($1\times10^5$ cells) were plated in each well of a 24-well plate in 500 µL DMEM/F12 containing 10% FBS and incubated at 37° C. and 5% $CO_2$. 500 µL saline or LMWF-5A+/−IL-1β (R&D Systems, Minneapolis, Minn.) or TNFα (ThermoFisher Scientific, Waltham, Mass.) (final concentration of 10 ng/mL) were added, and the cells were treated for 2, 4, 8, 12, or 24 h before harvesting for RNA or protein. For the evaluation of prostaglandin release, HSF-OAs were plated and treated as above. After 24 h, the media was collected, treated if necessary (as described below), and stored frozen until use.

Quantitative Real-Time PCR (qPCR) for COX2

RNA was isolated from the treated HSF-OAs using the miRNeasy kit (Qiagen, Valencia, Calif.), with 1 min of vortexing for homogenization. 0.5 µg of total RNA was then reverse transcribed into cDNA with the Qiagen QuantiTect kit. qPCR was then performed in duplicate using SYBR Green I Master Mix (Roche Diagnostics, Indianapolis, Ind.), a $RT^2$ qPCR primer assay for COX2 (Qiagen), and a QuantiTect primer assay for 18S rRNA (Qiagen) on a Roche 480 Lightcycler. Relative gene expression was calculated using the comparative threshold cycle ($\Delta\Delta C_T$) method versus a 0 h untreated control, with normalization to 18S rRNA expression.

COX2 Western Blot Analysis

HSF-OAs, as plated above, were lysed in 50 µL lysis buffer (Qproteome Mammalian Protein kit; Qiagen) according to manufacturer's instructions and centrifuged at 12,000×g at 4° C. for 10 min to remove the cellular debris. Lysates were prepared for western blot analysis by boiling in Bolt Reducing Buffer and Bolt LDS Sample Buffer (ThermoFisher Scientific, Waltham, Mass.). The lysates were separated by SDS-PAGE (8%) and subjected to western blot analysis using an anti-COX2 rabbit monoclonal primary antibody (1:1,000, ab62331; Abcam, Cambridge, Mass.) and a goat anti-rabbit IgG secondary antibody (1:10,000, Cat #7074P2, Cell Signaling, Danvers, Mass.). The COX2 protein levels were normalized to α-tubulin after stripping and reprobing with Reblot Plus (Millipore, Billerica, Mass.) and a horseradish peroxidase-conjugated α-tubulin antibody (1:5,000, DM1A, Cat #123515, Cell Signaling, Danvers, Mass.), respectively.

Prostaglandin Enzyme-Linked Immunosorbent Assays (ELISAs)

The levels of PGE2 in the media were analyzed using the Abcam Prostaglandin E2 ELISA kit (Cambridge, Mass.) following the manufacturer's protocol. The levels of PGD2 in the media were analyzed using the Cayman Chemical Prostaglandin D2-MOX EIA kit (Ann Arbor, Mich.) following the manufacturer's instructions. Notably, with this kit, the PGD2 in the sample is stabilized upon a 30-min incubation at 60° C. with a methyloximating reagent immediately following sample collection.

Statistical Analysis

All graphs and figures represent four independent experiments. Graphs represent the mean±standard error of the mean (SEM), and p-values were calculated using a standard student's paired two-tailed t-test.

Results:

LMWF of HSA Increases COX2 in Cytokine-Stimulated OA Synoviocytes

Figure 1C:
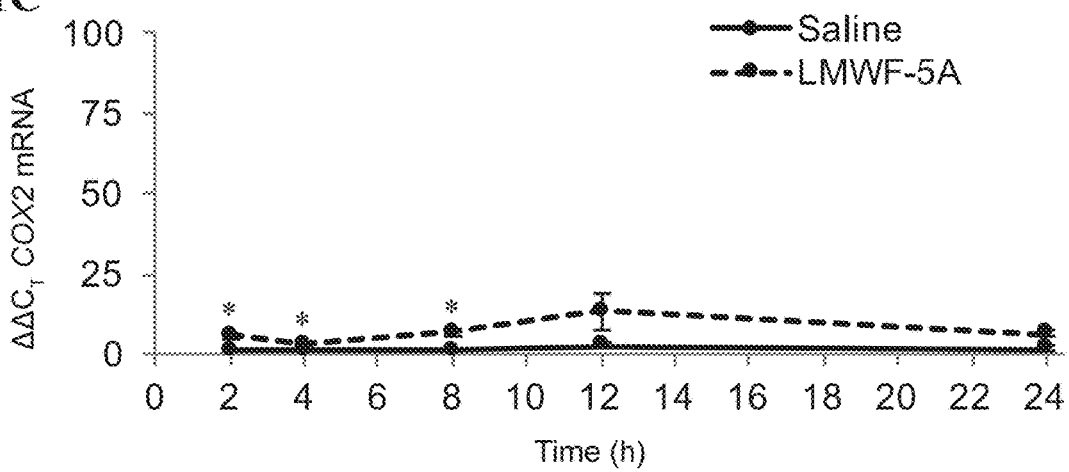
Figure 2:
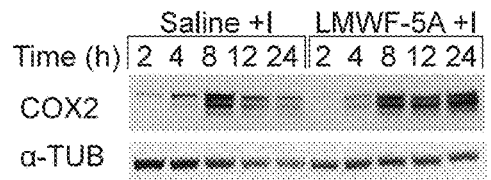
FIGS. 2A-2F show that the LMWF of HSA increases COX2 protein in OA synoviocytes when co-stimulated with pro-inflammatory cytokines. Western blots of protein lysates from OA synoviocytes were probed with antibodies against COX2 and the loading control α-Tubulin (FIGS. 2A, 2C, 2E). Relative band densities were graphed over time (FIGS. 2B, 2D, 2F). OA synoviocytes were stimulated with 10 ng/mL IL-1β (A, B), 10 ng/mL TNFα (FIGS. 2C, 2D), or left unstimulated (FIGS. 2E, 2F) in the presence of saline or LMWF-5A over a 24 h time course, and protein lysates were prepared at 2, 4, 8, 12, and 24 h. The normalized COX2 protein level (mean±SEM) is shown. * indicates significantly increased COX2 mRNA when compared to the saline control at that time point ($p<0.05$; $n=4$).
Figure 2B:
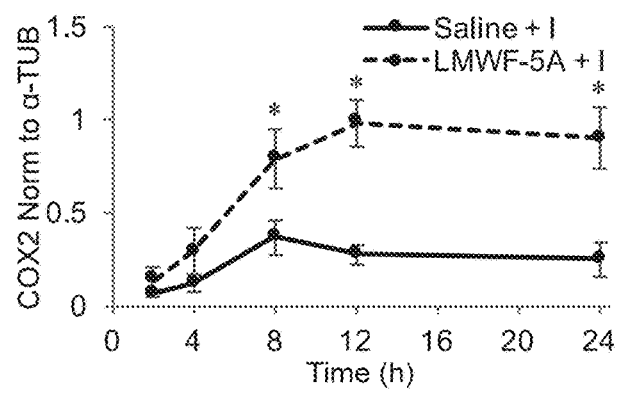
Figure 2C:
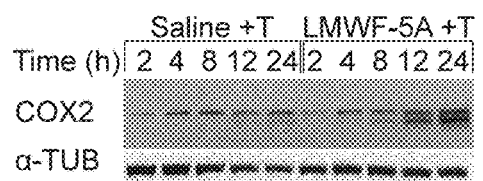
Figure 2D:
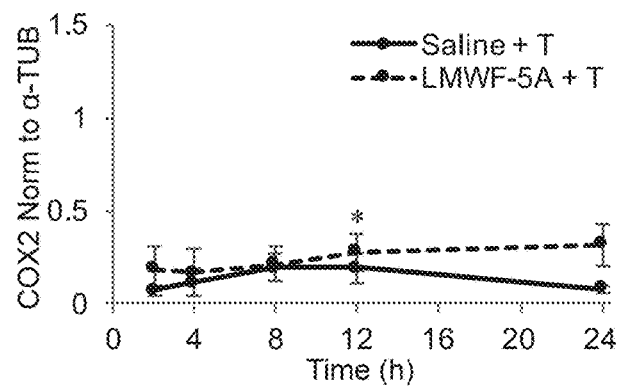
Figure 2E:
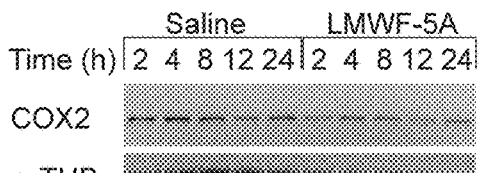
Figure 2F:
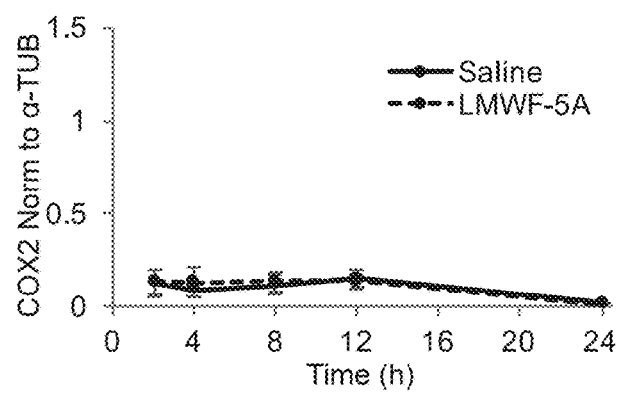

LMWF of HSA inhibits cytokine release in vitro (Thomas G W, et al., Anti-Inflammatory Activity in the Low Molecular Weight Fraction of Commercial Human Serum Albumin (LMWF5A). *J Immunoassay Immunochem* 2016, 37(1):55-67; Bar-Or D., et al., Commercial human albumin preparations for clinical use are immunosuppressive in vitro. *Crit Care Med* 2006, 34(6):1707-1712), and clinical trial results support an anti-inflammatory mode of action in vivo (Bar-Or D, et al., A randomized clinical trial to evaluate two doses of an intra-articular injection of LMWF-5A in adults with pain due to osteoarthritis of the knee. *PLoS One* 2014, 9(2): e87910). The mode of action of NSAIDs is to inhibit COX2 function and subsequent PG production (Botting R M. Vane's discovery of the mechanism of action of aspirin changed our understanding of its clinical pharmacology. *Pharmacol Rep* 2010, 62(3):518-525), thus, LMWF of HSA may function by a similar mechanism. Using primary synoviocytes isolated from the knee synovial membrane of patients with OA, COX2 mRNA was quantified by qPCR and COX2 protein by western blotting over a 24 h time course. HSF-OAs treated with saline and then stimulated with IL-1β or TNFα showed an induction in COX2 mRNA of 19 to 327-fold when normalized back to untreated cells over a 24 h time period (FIGS. 1A and B). Surprisingly, over the same time course, HSF-OAs stimulated with IL-1β or TNFα induced COX2 mRNA expression 52 to 692-fold, an additional ~1.2 to ~4.0-fold higher, in the presence of LMWF of HSA (FIGS. 1A and B; p<0.05 for LMWF-5A+IL-1β at 8, 12, and 24 h and LMWF-5A+TNFα at 2, 4, 8, 12, and 24 h). HSF-OAs incubated with LMWF of HSA without cytokine also showed an increase in COX2 mRNA of 3 to 13-fold when normalized back to untreated controls over a 24 h time course (FIG. 1C; p<0.05 for LMWF-5A at 2, 4, and 8 h). Interestingly, when COX2 protein was measured by western blot, significant fold increases in COX2 protein were only observed when OA synoviocytes were stimulated with cytokine in the presence of LMWF of HSA (FIG. 2). IL-1β-stimulated, LMWF of HSA-treated cells displayed significantly higher levels of COX2 protein between 8-24 hours (FIG. 2A; p<0.05 for LMWF-5A+IL-1β at 8, 12, and 24 h). When stimulated with TNFα in the presence of LMWF of HSA, COX2 protein was significantly increased over TNFα-stimulated, saline-treated HSF-OAs at 12 h and approached significance (p<0.07) at 24 h post-cytokine exposure (FIG. 2B; p<0.05 for LMWF-5A+TNFα at 12 h). In contrast to the observed COX2 mRNA dynamics, there was no difference in COX2 protein without cytokine exposure in OA synoviocytes treated with either LMWF of HSA or saline (FIG. 2C). Thus, in OA synoviocytes, both COX2 mRNA and COX2 protein significantly increase only when these cells are stimulated with IL-1β or TNFα in the presence of LMWF of HSA.

LMWF-of HSA Increases Prostaglandin Release from Cytokine-Stimulated OA Synoviocytes Considering that COX2 expression is increased under inflammatory conditions in the presence of LMWF of HSA, downstream products of COX2 in this system were studied. Two products, PGE2 and PGD2 were focused on. PGE2 has been implicated in the initial phase of the innate immune response, the clearance of the insult, as well as in the promotion of tissue regeneration (Zhang Y, et al: TISSUE REGENERATION. Inhibition of the prostaglandin-degrading enzyme 15-PGDH potentiates tissue regeneration. *Science* 2015, 348(6240):aaa2340). PGD2 has been linked to the second phase, resolution and healing (Gilroy D W, et al. Inducible cyclooxygenase may have anti-inflammatory properties. *Nat Med* 1999, 5(6):698-701). As described above, OA synoviocytes were treated with saline as a control or LMWF of HSA with or without IL-1β or TNFα. The amount of each prostaglandin secreted into the media was determined with a specific competitive ELISA after 24 h of treatment (FIG. 3).

Figure 3A:
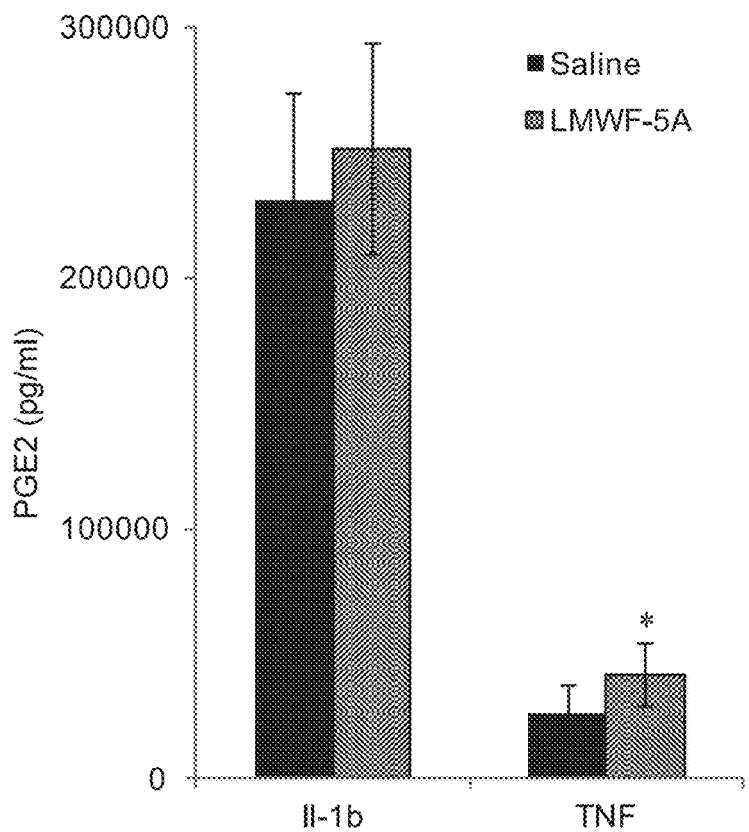
FIGS. 3A-3B show that the LMWF of HSA affects prostaglandin release by cytokine-stimulated OA synoviocytes. Cell culture media was collected from OA synoviocyte cultures 24 h after stimulation with either 10 ng/mL IL-1β or TNFα in the presence of saline or LMWF-5A. PGE2 (FIG. 3A) and PGD2 (FIG. 3B) were quantified by competitive ELISA. The mean concentration±SEM for four independent experiments were graphed, and * indicates a significant increase ($p<0.05$) in PG in the media when compared to the corresponding saline control.

The level of PGE2 in the media of cells treated solely with saline or LMWF of HSA was below the limit of detection (LOD) of this assay (39.1 pg/mL); however, when stimulated with cytokine, OA synoviocytes produced detectable levels of PGE2. Upon treatment with IL-1β or TNFα for 24 h under saline conditions, the media contained 231,000 pg/mL and 26,300 pg/mL of PGE2, respectively (FIG. 3A). When the cells were stimulated with IL-1β in the presence of LMWF of HSA, the concentration of PGE2 in the media (251,000 pg/mL) was not significantly different from that found in the media of IL-1β-stimulated cells in the presence of saline (FIG. 3A). In contrast, the level of PGE2 in the media of TNF-stimulated, LMWF of HSA-treated cells was increased by 37% (41,500 pg/mL, p<0.05) compared to that found in the media of TNF-stimulated, saline-treated cells (FIG. 3A).

Figure 3B:
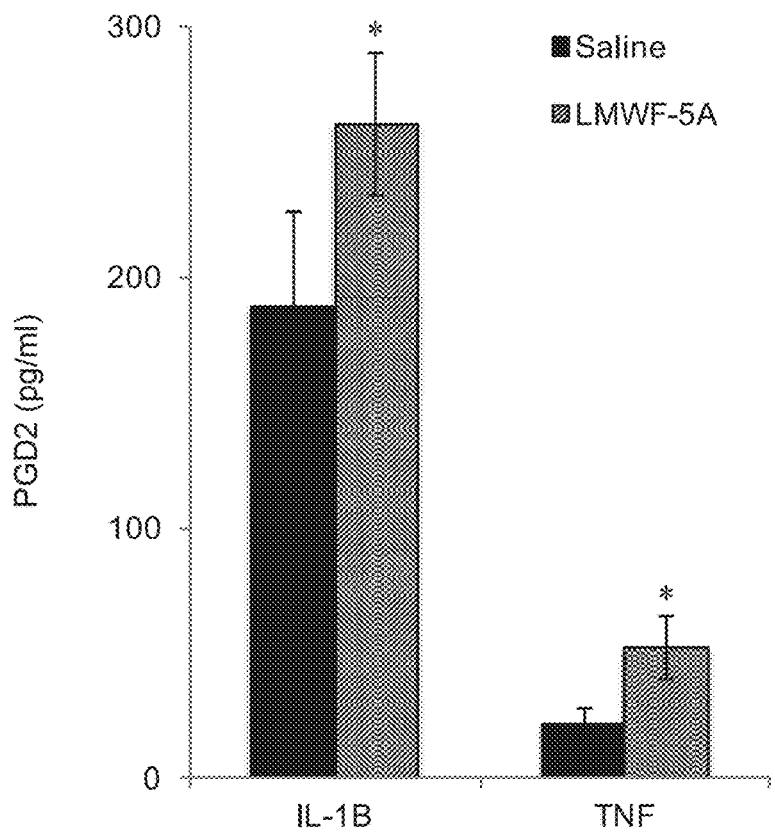
Figure 4:
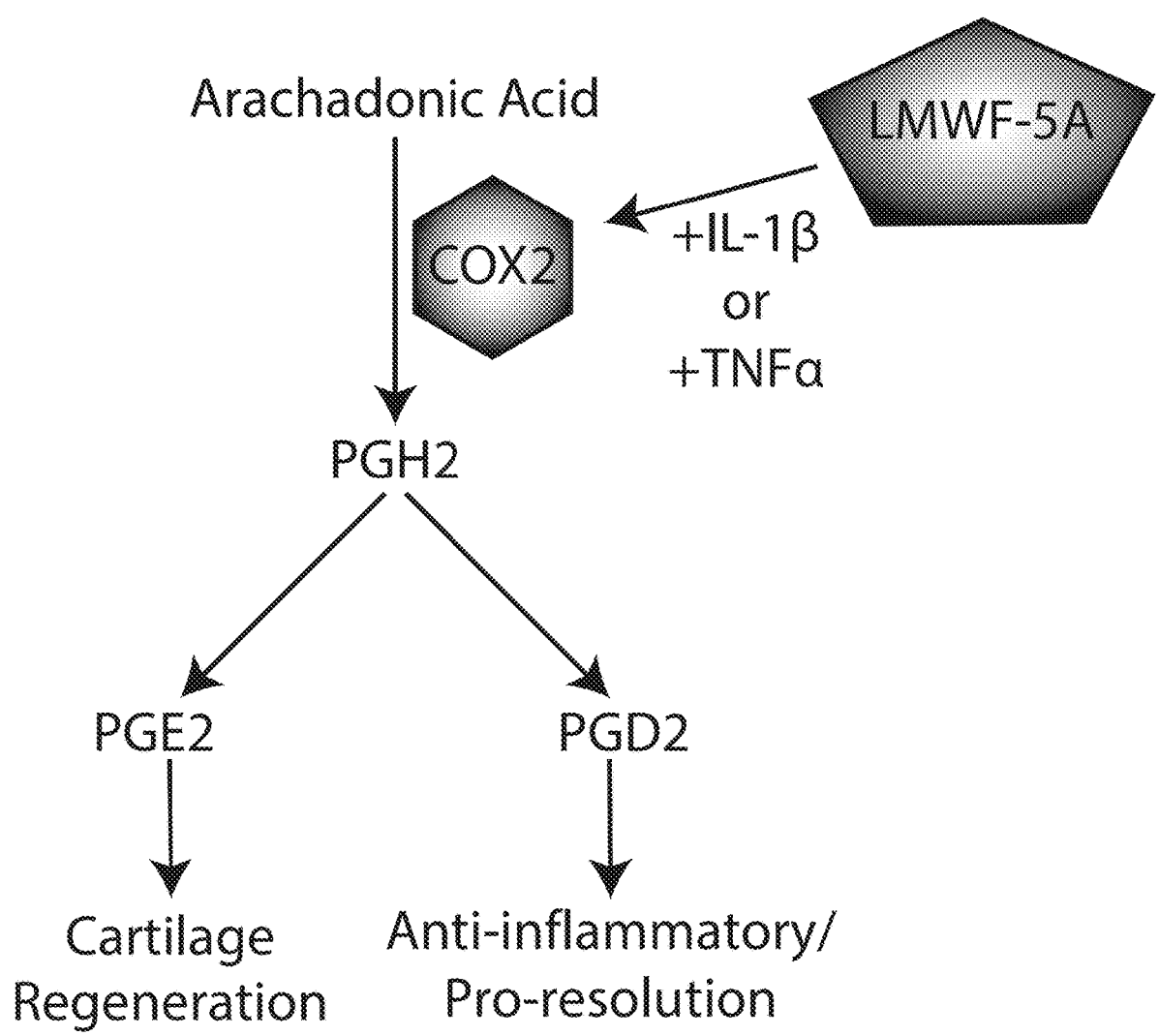
FIG. 4: Proposed mechanism of action for the LMWF of HSA with respect to the COX2 pathway.

Similar to PGE2, unstimulated OA synoviocytes exhibited no detectable release of PGD2 (LOD=2 pg/mL). Upon addition of IL-1β or TNFα to saline-treated cells, the concentration of PGD2 in the media increased to 189 pg/mL and 26.1 pg/mL, respectively (FIG. 3B). Interestingly, under these conditions, LMWF of HSA significantly increased the release of PGD2. When compared to cytokine-stimulated controls, PGD2 was 261 pg/mL with IL-1β stimulation and 52.4 pg/ml with TNFα stimulation, signifying 28% and 59% increases, respectively, in the presence of LMWF of HSA (p<0.05, FIG. 3B). It is important to note that PGE2 is a stable molecule, while PGD2 is unstable and must be chemically modified to prevent its degradation. Thus, in this experiment, the level of PGE2 reflects the accumulation of PGE2 over the 24 h time course, and the level of PGD2 represents a snapshot of the PGD2 release at the time of sample collection.

Example 2

This example demonstrates that LMWF of HSA wherein at least one of the components of the LMWF comprises DA-DKP exhibits a unique immune modulation pattern, disparate from both steroid or NSAID treatment. The enhancement of prostanoid release, specifically 15d-PGD$_2$, taken together with a drop in cytokine levels, may favor resolution.

The immune response is a carefully orchestrated series of events designed to counteract the initial insult then direct the clearance of debris and promote healing. Traumatic injury activates the innate immune system through the release of damage-associated molecular patterns or alarmins from injured tissues. Dysregulation can lead to systemic inflammatory response syndrome, multiple organ failure, and chronic inflammation. These patients frequently fall victim to "second hit" opportunistic infections as the result of a compensatory anti-inflammatory response. A better understanding of the innate immune response could help manage complications while allowing for proper immune progression. In this example, the ability of several classes of anti-inflammatory drugs to affect LPS induced cytokine and prostaglandin release from peripheral blood mononuclear cells (PBMC) was evaluated in vitro.

Methods for Example 2:
PBMC were cultured in the presence of anti-inflammatory compounds for one hour then stimulated with LPS. TNFα, PGE$_2$, and 15d-PGD$_2$ release was then determined by ELISA after 24 hours.

Figure 5:
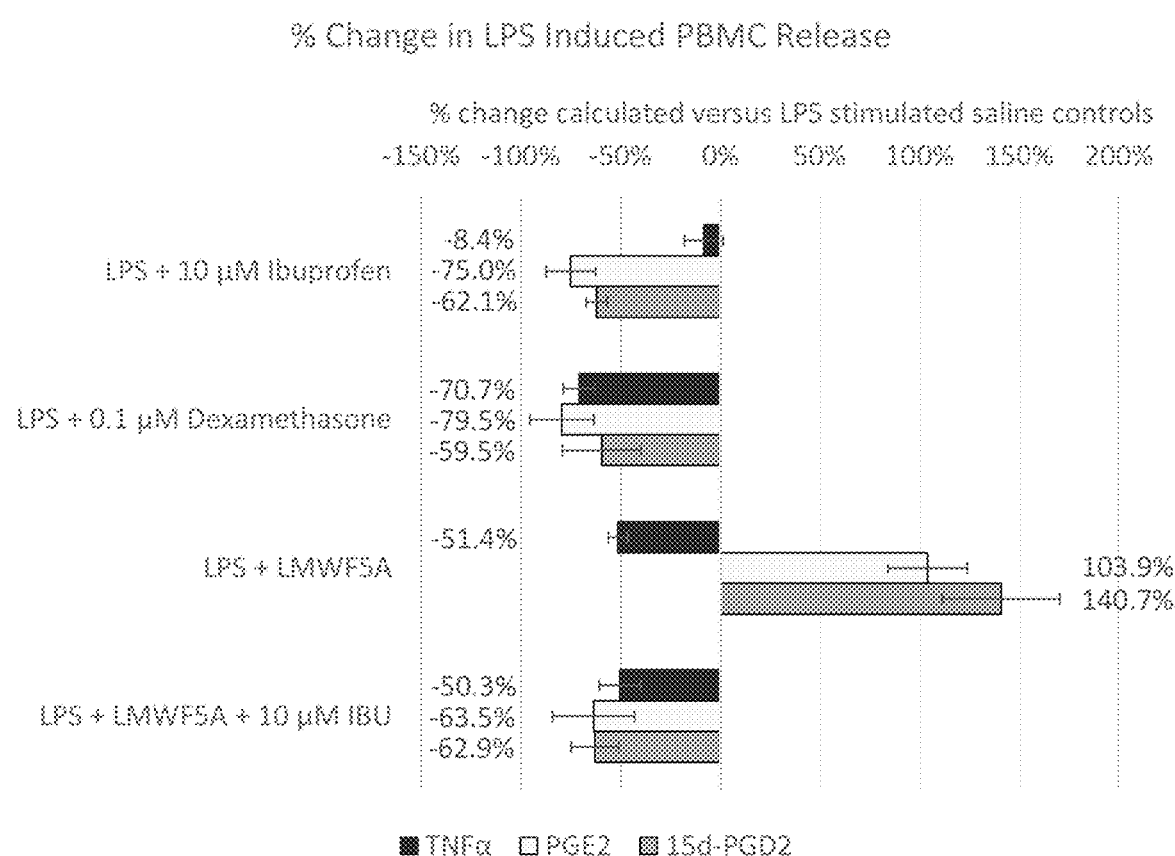
FIG. 5 shows the percent change in LPS induced PMBC Release as discussed in Example 2.

Results:
Three distinct immunomodulation patterns emerged following LPS stimulation of PBMC in the presence of various anti-inflammatories. Dexamethasone, a strong immunosuppressive steroid reduced both cytokine and prostanoid release. With the NSAID, ibuprofen, an almost complete attenuation of prostanglandin release was observed while cytokine levels remained unchanged. The LMWF of HSA exhibited an ability to reduce TNFα release while enhancing the amount PGE$_2$ and 15d-PGD2 detected. Incubating LMFW of HSA together with ibuprofen negated the observed prostanoid enhancement without effecting the suppression of TNFα. See FIG. 5.

Example 3

The data in this example demonstrate that LMWF of HSA wherein at least one of the components of the LMWF comprises DA-DKP inhibits NFκB signaling on a global level through regulation of NFκB relevant transcripts and miRNA. Systemic administration of LMWF of HSA may thus ameliorate inflammation in trauma patients.

A major pathway stimulated by trauma-induced inflammation is the NFκB signaling network. NFκB signaling results in downstream cellular responses that include production of pro-inflammatory cytokines, such as IL-1β and TNFα. Systemic inflammation may promote multiple-organ failure during severe trauma, in which NFκB signaling plays a central role. Historically, severe trauma patients have been treated with HSA to decrease tissue edema and for fluid resuscitation.

Methods:
Human embryonic kidney cells (HEK-293T) expressing a luciferase reporter gene driven by four NFκB-response elements were treated with either saline control or LMWF of HSA in the presence of IL-1β or TNFα. Luciferase activity was measured 3 h following cytokine exposure and normalized for cell viability. Human synovial primary fibroblasts (HSF-OA) were also used. To determine differential gene expression, RNA sequencing of whole transcriptome and miRNA expression was performed on HSF-OA either treated with saline or LMWF of HSA for 24 h with or without IL-1β stimulation. Significantly differentially expressed transcripts were identified in saline versus saline+IL-1β (SvS+I) and LMWF of HSA versus LMWF of HSA+IL-1β (LvL+I). Ingenuity® Pathway Analysis (IPA) was used to determine relevant gene networks differentially regulated by LMWF of HSA versus saline in IL-1β-stimulated cells.

Results:
In TNFα-stimulated HEK-293T cells, NFκB transcriptional activity was decreased by ~30% in LMWF of HSA treated cells. A known transcriptional target gene of NFκB, Interleukin-8 (IL-8) was differentially induced when comparing SvS+I and LvL+I gene lists, indicating a ~700-fold decrease in IL-8 mRNA induction in the presence of LMWF of HSA. Differential expression of several mediators of NFκB signaling were also observed, including NFκB inhibiting kinase (NIK), NFκB2, and RELB, all members of the non-canonical NFκB pathway. All of these transcripts decreased or did not increase in the presence of LMWF of HSA versus saline when cells were stimulated with IL-1β.

Furthermore, treatment with LMWF of HSA completely blocked expression of miR-486. By repressing negative NFκB feedback loops, miR-486 perpetuates NFκB signaling, lending more support to LMWF of HSA inhibition of NFκB signaling.

All of the documents cited herein are incorporated herein by reference.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

What is claimed is:

1. A method of inhibiting inflammation, the method comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about 6 hours after administration of the pharmaceutical composition.

2. The method of claim 1, wherein the LMWF of HSA contains components having a molecular weight of less than 5000 Da.

3. The method of claim 1, wherein the LMWF of HSA contains components having a molecular weight less than 3000 Da.

4. The method of claim 1, wherein at least one of the components in the LMWF of HSA comprises DA-DKP.

5. The method of claim 1, wherein the LMWF of HSA comprises one or more compounds selected from the group consisting of N-acetyl tryptophan and caprylic acid.

6. The method of claim 1, wherein the individual receiving the pharmaceutical composition is not administered a COX-2 antagonist within a time period of at least about 10 days prior to administration of the pharmaceutical composition.

7. The method of claim 1, wherein the individual receiving the pharmaceutical composition is not administered a COX-2 antagonist during the period of time in which at least one active ingredient in the pharmaceutical composition exerts its effect.

8. The method of claim 1, wherein the individual receiving the pharmaceutical composition is not administered a COX-2 antagonist within a time period of at least about two months after administration of a pharmaceutical composition of the invention.

9. The method of claim 1, wherein the COX-2 antagonist is selected from the group consisting of acetylsalicylic acid (aspirin), 2-(4-isobutylphenyl)propanoic acid (ibuprofen), N-(4-hydroxyphenyl)ethanamide (paracetamol), (S)-6-methoxy-α-methyl-2-naphthaleneacetic acid (naproxen), 2-[(2,6-dichlorophenyl)amino] benzeneacetic acid (diclofenac), 4-[5-(4-methylphenyl)-3-(trifluoromethyl)-1H-pyrazol-1-yl] benzenesulfonamide (celecoxib), 4-[4-(methylsulfonyl)phenyl]-3-phenyl-2(5H)-furanone (rofecoxib), and 4-(5-Methyl-3-phenylisoxazol-4-yl)benzolsulfonamid (valdecoxib).

10. A method of treating a T-cell mediated disease, the method comprising administering to an individual in need thereof an effective amount of a pharmaceutical composition comprising a low molecular weight fraction (LMWF) of human serum albumin (HSA), wherein the individual is not administered a cyclooxygenase-2 (COX-2) antagonist within the period of time ranging from about one hour before to about six hours after administration of the pharmaceutical composition.

11. The method of claim 10, wherein the T-cell mediated disease is graft rejection, graft versus host disease, an unwanted delayed-type hypersensitivity reaction, a T-cell mediated pulmonary disease, an autoimmune disease or an inflammatory disease.

12. The method of claim 10, wherein the T-cell-mediated disease is selected form the group consisting of multiple sclerosis, neuritis, polymyositis, psoriasis, vitiligo, Sjogren's syndrome, rheumatoid arthritis, Type 1 diabetes, autoimmune pancreatitis, inflammatory bowel diseases, Crohn's disease, ulcerative colitis, celiac disease, glomerulonephritis, scleroderma, sarcoidosis, autoimmune thyroid diseases, Hashimoto's thyroiditis, Graves disease, myasthenia gravis, Addison's disease, autoimmune uveoretinitis, pemphigus vulgaris, primary biliary cirrhosis, pernicious anemia and systemic lupus erythematosis.

13. The method of claim 10, wherein the T-cell-mediated disease is pulmonary fibrosis or idiopathic pulmonary fibrosis.

14. The method of claim 10, wherein the T-cell-mediated disease is an inflammatory disease.

15. The method of claim 10, wherein the LMWF of HSA contains components having a molecular weight of less than 5000 Da.

16. The method of claim 10, wherein the LMWF of HSA contains components having a molecular weight less than 3000 Da.

17. The method of claim 10, wherein at least one of the components in the LMWF of HSA comprises DA-DKP.

18. The method of claim 10, wherein the LMWF of HSA comprises one or more compounds selected from the group consisting of N-acetyl tryptophan and caprylic acid.

19. The method of claim 10, wherein the individual receiving the pharmaceutical composition is not administered a COX-2 antagonist within a time period of at least about 10 days prior to administration of the pharmaceutical composition.

20. The method of claim 10, wherein the individual receiving the pharmaceutical composition is not administered a COX-2 antagonist during the period of time in which at least one active ingredient in the pharmaceutical composition exerts its effect.

21. The method of claim 10, wherein the individual receiving the pharmaceutical composition is not administered a COX-2 antagonist within a time period of at least about two months after administration of a pharmaceutical composition of the invention.

22. The method of claim 10, wherein the COX-2 antagonist is selected from the group consisting of acetylsalicylic acid (aspirin), 2-(4-isobutylphenyl)propanoic acid (ibuprofen), N-(4-hydroxyphenyl)ethanamide (paracetamol), (S)-6-methoxy-α-methyl-2-naphthaleneacetic acid (naproxen), 2-[(2,6-dichlorophenyl)amino] benzeneacetic acid (diclofenac), 4-[5-(4-methylphenyl)-3-(trifluoromethyl)-1H-pyrazol-1-yl] benzenesulfonamide (celecoxib), 4-[4-(methyl sulfonyl)phenyl]-3-phenyl-2(5H)-furanone (rofecoxib), and 4-(5-Methyl-3-phenylisoxazol-4-yl)benzolsulfonamid (valdecoxib).

23. A method of treating an individual for a degenerative joint disease, the method comprising administering to an individual in need thereof an effective amount of a pharmaceutical composition comprising a LMWF of HSA, wherein the LMWF of HSA comprises DA-DKP, N-acetyl tryptophan and caprylic acid, wherein the individual is not administered a COX-2 antagonist within the period of time ranging from about 48 hours before to about 48 hours after administration of the pharmaceutical composition, wherein the individual receiving the pharmaceutical composition is not administered a COX-2 antagonist during the period of time in which at least one active ingredient in the pharmaceutical composition exerts its effect.

24. The method of claim 23, wherein the LMWF of HSA contains components having a molecular weight of less than 5000 Da.

25. The method of claim 23, wherein the LMWF of HSA contains components having a molecular weight less than 3000 Da.

26. The method of claim 23, wherein the individual receiving the pharmaceutical composition is not administered a COX-2 antagonist within a time period of at least about 10 days prior to administration of the pharmaceutical composition.

27. The method of claim 23, wherein the individual receiving the pharmaceutical composition is not administered a COX-2 antagonist within a time period of at least about two months after administration of a pharmaceutical composition of the invention.

28. The method of claim 23, wherein the COX-2 antagonist is selected from the group consisting of acetylsalicylic acid (aspirin), 2-(4-isobutylphenyl)propanoic acid (ibuprofen), N-(4-hydroxyphenyl)ethanamide (paracetamol), (S)-6-methoxy-α-methyl-2-naphthaleneacetic acid (naproxen), 2-[(2,6-dichlorophenyl)amino] benzeneacetic acid (diclofenac), 4-[5-(4-methylphenyl)-3-(trifluoromethyl)-1H-pyrazol-1-yl] benzenesulfonamide (celecoxib), 4-[4-(methylsulfonyl)phenyl]-3-phenyl-2(5H)-furanone (rofecoxib), and 4-(5-Methyl-3-phenylisoxazol-4-yl)benzolsulfonamid (valdecoxib).

29. The method of reducing the level of IL-8 in an individual, the method comprising administering to an individual in need thereof an effective amount of a pharmaceutical composition comprising a LMWF of HSA, wherein the individual is not administered a COX-2 antagonist within the period of time ranging from about one hour before to about six hours after administration of the pharmaceutical composition.

* * * * *